(12) United States Patent
Matsumoto et al.

(10) Patent No.: US 6,376,710 B2
(45) Date of Patent: Apr. 23, 2002

(54) AMIDINE COMPOUNDS AND THEIR USE AS PESTICIDES

(75) Inventors: Osamu Matsumoto; Toru Uekawa, both of Toyonaka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/818,789

(22) Filed: Mar. 28, 2001

(30) Foreign Application Priority Data

Mar. 28, 2000 (JP) ............................................. 12-088789

(51) Int. Cl.$^7$ ..................... C07C 257/10; C07C 257/18; A01M 13/00; A01M 19/00
(52) U.S. Cl. ..................... 564/244; 564/245; 564/246; 43/125; 43/127
(58) Field of Search ................................ 564/244, 245, 564/246; 43/125, 127, 129, 131, 134

(56) References Cited

U.S. PATENT DOCUMENTS

| | | | |
|---|---|---|---|
| 3,867,448 A | | 2/1975 | Duerr et al. |
| 3,875,230 A | * | 4/1975 | Pissiotas |
| 4,093,655 A | * | 6/1978 | Miller et al. |
| 4,163,056 A | * | 7/1979 | Kristiansen et al. |
| 4,670,593 A | | 6/1987 | Teach |
| 5,866,612 A | | 2/1999 | Oplinger et al. |

FOREIGN PATENT DOCUMENTS

| | | |
|---|---|---|
| JP | 5857357 A | 4/1983 |
| JP | 03264557 A | 11/1991 |

* cited by examiner

Primary Examiner—Johann Richter
Assistant Examiner—Sikarl A. Witherspoon
(74) Attorney, Agent, or Firm—Birch Stewart Kolasch & Birch LLP

(57) ABSTRACT

The present invention provides novel amidine compounds and novel pesticides containing these amidine compounds as active ingredients. The amidine compounds are expressed by formula I:

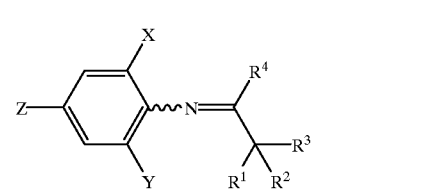

wherein X and Y are the same or different and are independently halogen, nitro, cyano, or $C_1$–$C_6$ alkyl; Z is $C_1$–$C_6$ haloalkyl or $C_1$–$C_6$ haloalkoxy; $R^1$ is hydrogen, halogen, $C_1$–$C_6$ alkyl, $C_1$–$C_6$ haloalkyl, $C_1$–$C_6$ alkoxy, $C_1$–$C_6$ haloalkoxy, or a group of formula: $S(O)_n$—$R^5$ (wherein $R^5$ is $C_1$–$C_6$ alkyl or $C_1$–$C_6$ haloalkyl; and n is 0, 1, or 2); $R^2$ and $R^3$ are the same or different and are independently halogen or $C_1$–$C_6$ haloalkyl; and $R^4$ is a group of formula: $NR^6R^7$ or $N=CR^8R^9$ (wherein $R^6$ is hydrogen, $C_1$–$C_6$ alkyl, ($C_1$–$C_6$ alkoxy)-carbonyl, ($C_1$–$C_6$ alkoxy) $C_1$–$C_6$ alkyl, or $C_2$–$C_6$ acyl; $R^7$ is hydrogen, $C_1$–$C_6$ alkyl, ($C_1$–$C_6$ alkoxy) carbonyl, or $C_2$–$C_6$ acyl; $R^8$ is $C_1$–$C_6$ alkyl or hydrogen; and $R^9$ is $C_1$–$C_6$ alkoxy, $C_1$–$C_6$ alkyl, or di($C_1$–$C_6$ alkyl)amino).

8 Claims, No Drawings

AMIDINE COMPOUNDS AND THEIR USE AS PESTICIDES

FIELD OF INVENTION

The present invention relates to amidine compounds and their use as pesticides.

BACKGROUND OF THE INVENTION

Various pesticides have been used for the control of pests including harmful insects, acarines, and nematodes. There have been drastic changes in the control of pests, such as development of new control systems for labor-saving, necessity for paying attention to influences on the environment, and occurrence of resistance to chemical agents in the target pests. Accordingly, development of chemical agents with novel structure or mechanism of action has been eagerly desired. An objective of the present invention is to provide novel compounds having insecticidal, acaricidal, and nematocidal activity, as well as novel pesticides containing these compounds as active agents.

SUMMARY OF THE INVENTION

Under these circumstances, the present inventors have extensively studied. As a result, they have found that amidine compounds of formula I as depicted below have excellent pesticidal effects, i.e., insecticidal, acaricidal, and nematocidal activity, thereby completing the present invention.

Thus the present invention provides amidine compounds of formula I (hereinafter referred to as the present compound(s)):

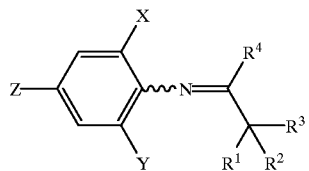

I wherein X and Y are the same or different and are independently halogen, nitro, cyano, or $C_1$–$C_6$ alkyl; Z is $C_1$–$C_6$ haloalkyl or $C_1$–$C_6$ haloalkoxy; $R^1$ is hydrogen, halogen, $C_1$–$C_6$ alkyl, $C_1$–$C_6$ haloalkyl, $C_1$–$C_6$ alkoxy, $C_1$–$C_6$ haloalkoxy, or a group of formula: $S(O)_n$—$R^5$ (wherein $R^5$ is $C_1$–$C_6$ alkyl or $C_1$–$C_6$ haloalkyl; and n is 0, 1, or 2); $R^2$ and $R^3$ are the same or different and are independently halogen or $C_1$–$C_6$ haloalkyl; and $R^4$ is a group of formula: $NR^6R^7$ or $N=CR^8R^9$ (wherein $R^6$ is hydrogen, $C_1$–$C_6$ alkyl, ($C_1$–$C_6$ alkoxy)-carbonyl, ($C_1$–$C_6$ alkoxy) $C_1$–$C_6$ alkyl, or $C_2$–$C_6$ acyl; $R^7$ is hydrogen, $C_1$–$C_6$ alkyl, ($C_1$–$C_6$ alkoxy)carbonyl, or $C_2$–$C_6$ acyl; $R^8$ is $C_1$–$C_6$ alkyl or hydrogen; and $R^9$ is $C_1$–$C_6$ alkoxy, $C_1$–$C_6$ alkyl, or di($C_1$–$C_6$ alkyl)amino); and pesticides containing these amidine compounds as active ingredients.

DETAILED DESCRIPTION OF THE INVENTION

Specific examples of the substituents in the present compounds are as follows.

The "halogen" may include fluorine, chlorine, and bromine atoms.

The "$C_1$–$C_6$ alkyl" may include methyl, ethyl, propyl, isopropyl, butyl, isobutyl, sec-butyl, tert-butyl, pentyl, neopentyl, and hexyl groups.

The "$C_1$–$C_6$ haloalkyl" may include trifluoromethyl, pentafluoroethyl, heptafluoropropyl, nonafluorobutyl, difluoromethyl, chlorodifluoromethyl, dichlorofluoromethyl, bromodifluoromethyl, dibromofluoromethyl, chlorofluoromethyl, bromofluoromethyl, dichloromethyl, 2-chlorotetrafluoroethyl, 2-bromotetrafluoroethyl, and 2,2,2-trifluoroethyl groups.

The "$C_1$–$C_6$ haloalkoxy" may include trifluoromethoxy, pentafluoroethoxy, and difluoromethoxy groups.

The "($C_1$–$C_6$ alkoxy)carbonyl" may include methoxycarbonyl and ethoxycarbonyl groups.

The "($C_1$–$C_6$ alkoxy) $C_1$–$C_6$ alkyl" may include methoxymethyl, ethoxymethyl, propoxymethyl, isopropoxymethyl, butoxymethyl, isobutoxymethyl, 2-methoxyethyl, 1-methoxy-2,2-dimethylpropyl, 1-ethoxy-2,2-dimethylpropyl, 1-methoxy-1,2,2-trimethylpropyl and 1-ethoxy-1,2,2-trimethylpropyl groups.

The "$C_2$–$C_6$ acyl", referring also to ($C_1$–$C_5$ alkyl) carbonyl, may include acetyl, propanoyl, butanoyl, 3-methylbutanoyl, 2-methylpropanoyl, and pentanoyl groups.

The "$C_1$–$C_6$ alkoxy" may include methoxy, ethoxy, propoxy, isopropoxy, butoxy, isobutoxy, sec-butoxy, and tert-butoxy groups.

The "di($C_1$–$C_6$ alkyl)amino" may include dimethylamino, ethyl(methyl)amino, diethylamino, and dipropylamino groups.

Preferred substituents in the present compounds from the viewpoints of high insecticidal and acaricidal activity are as follows:

Each of X and Y may preferably be a halogen atom or a nitro group;

Z may preferably be a $C_1$–$C_6$ haloalkyl group, specifically a trifluoromethyl group;

$R^1$ may preferably be a $C_1$–$C_6$ haloalkyl group;

Each of $R^2$ and $R^3$ may preferably be a halogen atom;

$R^4$ may preferably be an amino group.

The following will describe some production processes for the present compounds. The present compounds can be produced, for example, by one of production processes 1 to 5 as described below.

Production Process 1

The present compounds wherein $R^4$ is a group of formula: $NR^6R^7$ can be produced by reacting a compound of formula II:

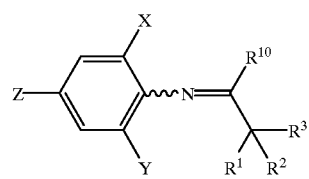

II wherein X, Y, Z, $R^1$, $R^2$, and $R^3$ are as defined above; and $R^{10}$ is halogen (e.g., chlorine, bromine, iodine), with a compound of formula III:

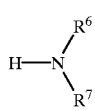

wherein $R^6$ and $R^7$ are as defined above, or a salt thereof in the presence of a base without any solvent or in a solvent.

The reaction is usually carried out at a temperature of about −5° C. to 150° C. for 1 minute to 24 hours. The amounts of reagents to be used in the reaction are usually 1 to 10 moles of compound III or a salt thereof and 1 to 10 moles of a base, relative to 1 mole of compound II. When compound III is allowed to act by itself as a base, this compound may be used in an amount of 2 mole to an excessive amount.

The base may include inorganic bases such as sodium hydride, potassium hydride, sodium hydroxide, potassium hydroxide, sodium carbonate, and potassium carbonate; alkali metal alkoxides such as sodium methoxide and sodium ethoxide; and tertiary amines such as triethylamine.

The solvent which can be used in the reaction may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitrites such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

After completion of the reaction, the reaction mixture is poured into water, followed by post-treatment including, for example, extraction with an organic solvent and evaporation of the organic layer, to give a product of the desired present compound. The product may be purified by chromatography, recrystallization, or any other technique.

Compound II can be produced by reacting a compound of formula IV:

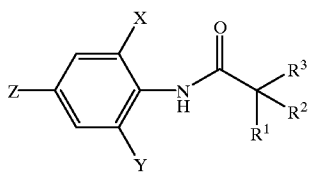

wherein X, Y, Z, $R^1$, $R^2$, and $R^3$ are as defined above, with a halogenating agent according to the known methods (see, e.g., JP-A 8-295663).

The halogenating agent may include phosphorus pentachloride, phosphorus oxychloride, and triphenylphosphine-carbon tetrachloride.

The reaction is usually carried out at a temperature of about −5° C. to 150° C. for 1 to 24 hours. The amounts of reagents to be used in the reaction are 1 mole to an excessive amount of a halogenating agent, relative to 1 mole of compound IV.

The solvent which can be used in the reaction may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, ethylene glycol dimethyl ether; acid amides such as N,N-dimethylformamide and N,N-dimethylacetamide; sulfur compounds such as dimethylsulfoxide and sulforane; and mixtures thereof.

After completion of the reaction, the reaction mixture is poured into water, followed by post-treatment including, for example, extraction with an organic solvent and evaporation of the organic layer, to give a product of the desired compound II. The product may be purified by chromatography, recrystallization, or any other technique.

Compound IV can be produced as shown in the following scheme:

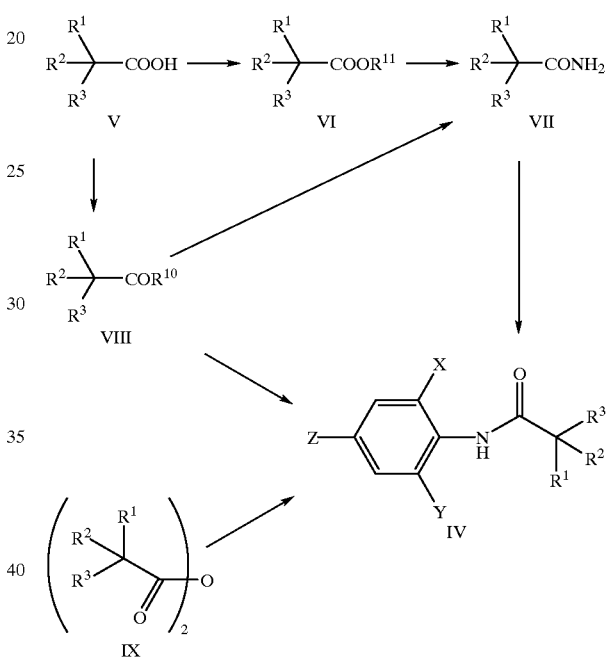

wherein X, Y, Z, $R^1$, $R^2$, $R^3$, and $R^{10}$ are as defined above; and $R^{11}$ is $C_1$–$C_6$ alkyl.

Ester compound VI can be produced from carboxylic acid compound V according to the known methods (see, e.g., J. Org. Chem. 55, 812 (1990); Tetrahedron 52, 157 (1996)).

Amide compound VII can be produced from ester compound VI according to the known methods (see, e.g., J. Org. Chem. 51, 332 (1986); Tetrahedron Lett. 34, 7195 (1993)).

Acid halide VIII can be produced from carboxylic acid compound I according to the known methods (see, e.g., J. Org. Chem. 54, 6096 (1989); J. Fluorine Chem. 75, 35 (1995)).

Amide compound III can be produced from acid halide IV according to the known methods (see, e.g., J. Org. Chem. 60, 1319 (1995); J. Fluorine Chem. 84, 135 (1997)).

Compound IV can be produced by reacting acid halide VIII with a compound of formula X:

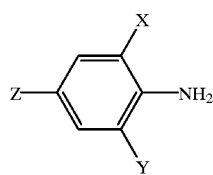

wherein X, Y, and Z are as defined above, according to the known methods (see, e.g., Shin-Jikken Kagaku Koza (Maruzen), vol. 14 [II], pp. 1142–1145).

Compound IV can be produced by reacting acid anhydride IX with compound X according to the known methods (see, e.g., JP-A 8-295663).

Compound IV can also be produced by reacting amide compound VII with a compound of formula XI:

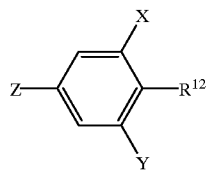

wherein X, Y, and Z are as defined above; and $R^{12}$ is a leaving group or atom (e.g., fluorine, chlorine, bromine, iodine, methoxy, trifluoromethylsulfonyloxy, methanesulfonyloxy), usually in the presence of a base in a solvent, and if necessary, in the presence of a catalyst.

The reaction is usually carried out at a temperature of about –5° C. to 150° C. for 10 minutes to 24 hours. The amounts of reagents to be used in the reaction are usually 1 to 10 moles of amide compound VII and 1 mole to a large excess of a base, relative to 1 mole of compound XI.

The base may include inorganic bases such as sodium hydride, potassium hydride, sodium hydroxide, potassium hydroxide, sodium carbonate, and potassium carbonate; alkali metal alkoxides such as sodium methoxide and sodium ethoxide; and tertiary amines such as triethylamine, pyridine, 4-dimethylaminopyridine, and N,N-dimethylaniline.

The solvent may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitrites such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

The catalyst which is used, if necessary, may include crown ethers and potassium fluoride.

After completion of the reaction, the reaction mixture is poured into water, followed by post-treatment including, for example, extraction with an organic solvent and evaporation of the organic layer, to give a product of the desired compound IV. The product may be purified by chromatography, recrystallization, or any other technique.

Production Process 2

The present compounds wherein $R^4$ is amino can be produced by reacting a compound of formula XI with a compound of formula XII:

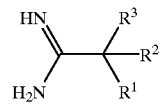

wherein $R^1$, $R^2$, and $R^3$ are as defined above, usually in the presence of a base in a solvent, and if necessary, in the presence of a catalyst.

The reaction is usually carried out at a temperature of –5° C. to 150° C. for 10 minutes to 24 hours. The amounts of reagents to be used in the reaction are usually 1 to 10 moles of compound XII and 1 mole to a large excess of a base, relative to 1 mole of compound XI.

The base may include inorganic bases such as sodium hydride, potassium hydride, sodium hydroxide, potassium hydroxide, sodium carbonate, and potassium carbonate; alkali metal alkoxides such as sodium methoxide and sodium ethoxide; and tertiary amines such as triethylamine, pyridine, 4-dimethylaminopyridine, and N,N-dimethylaniline.

The solvent may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitrites such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

The catalyst which is used, if necessary, may include crown ethers and potassium fluoride.

After completion of the reaction, the reaction mixture is poured into water, followed by post-treatment including, for example, extraction with an organic solvent and evaporation of the organic layer, to give a product of the desired present compound. The product may be purified by chromatography, recrystallization, or any other technique.

Compound XII can be produced according to the known methods (see, e.g., J. Org. Chem. 30, 3729 (1965)).

Production Process 3

The present compounds wherein $R^4$ is a group of formula: $NHR^{13}$ or $N(R^{13})_2$ and $R^{13}$ is $C_1$–$C_6$ alkyl, ($C_1$–$C_6$ alkoxy) carbonyl, ($C_1$–$C_6$ alkoxy) $C_1$–$C_6$ alkyl, or $C_2$–$C_6$ acyl can be produced by the present compounds wherein $R^4$ is amino (hereinafter referred to as compound A) with a compound of formula XIII:

$$R^{13}\text{—}R^{14} \quad\quad\quad \text{XIII}$$

wherein $R^{13}$ is as defined above and $R^{14}$ is a leaving group or atom (e.g., chlorine, bromine, iodine, trifluoromethylsulfonyloxy, methanesulfonyloxy), usually in the presence of a base in a solvent.

The reaction is usually carried out at a temperature of –5° C. to 150° C. for 1 to 24 hours.

When the present compounds wherein $R^4$ is a group of formula: $NHR^{13}$ are produced, the amounts of reagents to be used in the reaction are usually 0.8 to 1 mole of compound XIII and 0.8 to 10 moles of a base, relative to 1 mole of compound A.

When the present compounds wherein $R^4$ is a group of formula: $N(R^{13})_2$ are produced, the amounts of reagents to be used in the reaction are usually 2 to 10 mole of compound XIII and 2 to 10 moles of a base, relative to 1 mole of compound A.

The base may include inorganic bases such as sodium hydride, potassium hydride, sodium hydroxide, potassium hydroxide, sodium carbonate, and potassium carbonate; alkali metal alkoxides such as sodium methoxide and sodium ethoxide; and tertiary amines such as triethylamine, pyridine, 4-dimethylaminopyridine, and N,N-dimethylaniline.

The solvent which can be used in the reaction may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitriles such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

After completion of the reaction, the reaction mixture is poured into water, followed by post-treatment including, for example, extraction with an organic solvent and evaporation of the organic layer, to give a product of the desired present compound. The product may be purified by chromatography, recrystallization, or any other technique.

Production Process 4

The present compounds wherein $R^4$ is a group of formula: $NR^{13}R^{15}$, $R^{18}$ is as defined above, and $R^{15}$ is $C_1$–$C_6$ alkyl, ($C_1$–$C_6$ alkoxy)carbonyl, ($C_1$–$C_6$ alkoxy) $C_1$–$C_6$ alkyl, or $C_2$–$C_6$ acyl can be produced by the present compounds wherein $R^4$ is a group of formula: $NHR^{13}$ (hereinafter referred to as compound B) with a compound of formula XIV:

$$R^{15}\text{—}R^{14} \qquad \qquad \text{XIV}$$

wherein $R^{14}$ and $R^{15}$ are as defined above, usually in the presence of a base in a solvent.

The reaction is usually carried out at a temperature of $-5°$ C. to 150° C. for 1 to 24 hours. The amounts of reagents to be used in the reaction are usually 1 to 10 moles of compound XIV and 1 to 10 moles of a base, relative to 1 mole of compound B.

The base may include inorganic bases such as sodium hydride, potassium hydride, sodium hydroxide, potassium hydroxide, sodium carbonate, and potassium carbonate; alkali metal alkoxides such as sodium methoxide and sodium ethoxide; and tertiary amines such as triethylamine, pyridine, 4-dimethylaminopyridine, and N,N-dimethylaniline.

The solvent which can be used in the reaction may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitriles such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

After completion of the reaction, the reaction mixture is poured into water, followed by post-treatment including, for example, extraction with an organic solvent and evaporation of the organic layer, to give a product of the desired present compound. The product may be purified by chromatography, recrystallization, or any other technique.

Production Process 5

The present compounds wherein $R^4$ is a group of formula: $N\text{=}CR^8R^9$ can be produced by reacting compound A with a compound of formula XV:

$$(R^{16}O)_2CR^8R^9 \qquad \qquad \text{XV}$$

wherein $R^8$ and $R^9$ are as defined above and $R^{16}$ is $C_1$–$C_6$ alkyl, or a compound of formula XVI:

$$O\text{=}CR^8R^9 \qquad \qquad \text{XVI}$$

wherein $R^8$ and $R^9$ are as defined above, in the presence of an acid catalyst, without any solvent or in a solvent.

The reaction is usually carried out at a temperature of $-5°$ C. to 150° C. for 1 to 24 hours. The amounts of reagents to be used in the reaction are usually 1 to 10 moles of compound XV or XVI and 0.01 to 1 mole of an acid catalyst, relative to 1 mole of compound A.

The acid catalyst may include inorganic acids such as hydrochloric acid and sulfuric acid; organic acids such as acetic acid and p-toluenesulfonic acid; and aprotic acids such as boron trifluoride.

The solvent which can be used in the reaction may include aliphatic hydrocarbons such as hexane, heptane, ligroin, and petroleum ether; aromatic hydrocarbons such as toluene; halogenated hydrocarbons such as dichloroethane, chlorobenzene, and dichlorobenzene; ethers such as diisopropyl ether, dioxane, tetrahydrofuran, and ethylene glycol dimethyl ether; ketones such as acetone, methyl ethyl ketone, methyl isobutyl ketone, isophorone, and cyclohexanone; esters such as ethyl acetate and butyl acetate; nitriles such as acetonitrile and isobutyronitrile; nitro compounds such as nitroethane and nitrobenzene; acid amides such as formamide, N,N-dimethylformamide, and N,N-dimethylacetamide; sulfur compounds such as dimethylsulfoxide and sulforane; water; and mixtures thereof.

After completion of the reaction, the reaction mixture is poured into water, followed by post-treatment including, for example, extraction with an organic solvent and evaporation of the organic layer, to give a product of the desired present compound. The product may be purified by chromatography, recrystallization, or any other technique.

The present compounds may have structural isomers with respect to the double bond as depicted below, and both isomers are embraced by the present invention.

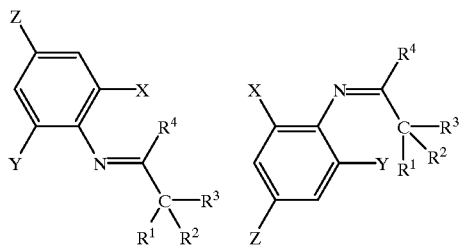

The present compounds wherein $R^4$ is a group of formula: $NR^6R^7$ and $R^6$ is hydrogen may have tautomers as depicted below, and these tautomers are embraced by the present invention.

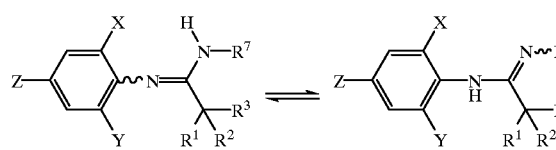

Specific examples of the present compounds are those listed in Tables 1 to 13 below.

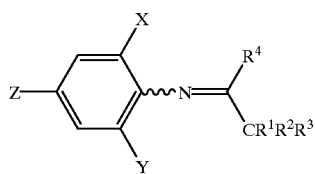

TABLE 1

| X | Y | Z | CR$^1$R$^2$R$^3$ | R$^4$ |
|---|---|---|---|---|
| Cl | Cl | CF$_3$ | CF$_3$ | NH$_2$ |
| NO$_2$ | NO$_2$ | CF$_3$ | CF$_3$ | NH$_2$ |
| Cl | NO$_2$ | CF$_3$ | CF$_3$ | NH$_2$ |
| Cl | F | CF$_3$ | CF$_3$ | NH$_2$ |
| Cl | CN | CF$_3$ | CF$_3$ | NH$_2$ |
| Cl | Br | CF$_3$ | CF$_3$ | NH$_2$ |
| Cl | Me | CF$_3$ | CF$_3$ | NH$_2$ |
| Cl | Et | CF$_3$ | CF$_3$ | NH$_2$ |
| NO$_2$ | F | CF$_3$ | CF$_3$ | NH$_2$ |
| NO$_2$ | CN | CF$_3$ | CF$_3$ | NH$_2$ |
| NO$_2$ | Br | CF$_3$ | CF$_3$ | NH$_2$ |
| NO$_2$ | Me | CF$_3$ | CF$_3$ | NH$_2$ |
| NO$_2$ | Et | CF$_3$ | CF$_3$ | NH$_2$ |
| F | F | CF$_3$ | CF$_3$ | NH$_2$ |
| F | CN | CF$_3$ | CF$_3$ | NH$_2$ |
| F | Br | CF$_3$ | CF$_3$ | NH$_2$ |
| F | Me | CF$_3$ | CF$_3$ | NH$_2$ |
| F | Et | CF$_3$ | CF$_3$ | NH$_2$ |
| CN | CN | CF$_3$ | CF$_3$ | NH$_2$ |
| CN | Br | CF$_3$ | CF$_3$ | NH$_2$ |
| CN | Me | CF$_3$ | CF$_3$ | NH$_2$ |
| CN | Et | CF$_3$ | CF$_3$ | NH$_2$ |
| Br | Br | CF$_3$ | CF$_3$ | NH$_2$ |

TABLE 2

| X | Y | Z | CR$^1$R$^2$R$^3$ | R$^4$ |
|---|---|---|---|---|
| Br | Me | CF$_3$ | CF$_3$ | NH$_2$ |
| Br | Et | CF$_3$ | CF$_3$ | NH$_2$ |
| Me | Me | CF$_3$ | CF$_3$ | NH$_2$ |
| Me | Et | CF$_3$ | CF$_3$ | NH$_2$ |
| Et | Et | CF$_3$ | CF$_3$ | NH$_2$ |
| Cl | Cl | CF$_3$ | C$_2$F$_5$ | NH$_2$ |
| NO$_2$ | NO$_2$ | CF$_3$ | C$_2$F$_5$ | NH$_2$ |
| Cl | NO$_2$ | CF$_3$ | C$_2$F$_5$ | NH$_2$ |
| Cl | F | CF$_3$ | C$_2$F$_5$ | NH$_2$ |
| Cl | CN | CF$_3$ | C$_2$F$_5$ | NH$_2$ |
| Cl | Br | CF$_3$ | C$_2$F$_5$ | NH$_2$ |
| Cl | Me | CF$_3$ | C$_2$F$_5$ | NH$_2$ |
| Cl | Et | CF$_3$ | C$_2$F$_5$ | NH$_2$ |
| NO$_2$ | F | CF$_3$ | C$_2$F$_5$ | NH$_2$ |
| NO$_2$ | CN | CF$_3$ | C$_2$F$_5$ | NH$_2$ |
| NO$_2$ | Br | CF$_3$ | C$_2$F$_5$ | NH$_2$ |
| NO$_2$ | Me | CF$_3$ | C$_2$F$_5$ | NH$_2$ |
| NO$_2$ | Et | CF$_3$ | C$_2$F$_5$ | NH$_2$ |
| F | F | CF$_3$ | C$_2$F$_5$ | NH$_2$ |
| F | CN | CF$_3$ | C$_2$F$_5$ | NH$_2$ |
| F | Br | CF$_3$ | C$_2$F$_5$ | NH$_2$ |
| F | Me | CF$_3$ | C$_2$F$_5$ | NH$_2$ |
| F | Et | CF$_3$ | C$_2$F$_5$ | NH$_2$ |

TABLE 3

| X | Y | Z | CR$^1$R$^2$R$^3$ | R$^4$ |
|---|---|---|---|---|
| CN | CN | CF$_3$ | C$_2$F$_5$ | NH$_2$ |
| CN | Br | CF$_3$ | C$_2$F$_5$ | NH$_2$ |
| CN | Me | CF$_3$ | C$_2$F$_5$ | NH$_2$ |
| CN | Et | CF$_3$ | C$_2$F$_5$ | NH$_2$ |
| Br | Br | CF$_3$ | C$_2$F$_5$ | NH$_2$ |
| Br | Me | CF$_3$ | C$_2$F$_5$ | NH$_2$ |
| Br | Et | CF$_3$ | C$_2$F$_5$ | NH$_2$ |
| Me | Me | CF$_3$ | C$_2$F$_5$ | NH$_2$ |
| Me | Et | CF$_3$ | C$_2$F$_5$ | NH$_2$ |
| Et | Et | CF$_3$ | C$_2$F$_5$ | NH$_2$ |
| Cl | Cl | CF$_3$ | CClF$_2$ | NH$_2$ |
| NO$_2$ | NO$_2$ | CF$_3$ | CClF$_2$ | NH$_2$ |
| Cl | Cl | CF$_3$ | CCl$_2$F | NH$_2$ |
| NO$_2$ | NO$_2$ | CF$_3$ | CCl$_2$F | NH$_2$ |
| Cl | Cl | CF$_3$ | C$_3$F$_7$ | NH$_2$ |
| NO$_2$ | NO$_2$ | CF$_3$ | C$_3$F$_7$ | NH$_2$ |
| Cl | Cl | CF$_3$ | C$_4$F$_9$ | NH$_2$ |
| NO$_2$ | NO$_2$ | CF$_3$ | C$_4$F$_9$ | NH$_2$ |
| Cl | Cl | CF$_3$ | C$_5$F$_{11}$ | NH$_2$ |
| NO$_2$ | NO$_2$ | CF$_3$ | C$_5$F$_{11}$ | NH$_2$ |
| Cl | Cl | CF$_3$ | C$_6$F$_{13}$ | NH$_2$ |
| NO$_2$ | NO$_2$ | CF$_3$ | C$_6$F$_{13}$ | NH$_2$ |
| Cl | Cl | CF$_3$ | CBrF$_2$ | NH$_2$ |

TABLE 4

| X | Y | Z | CR$^1$R$^2$R$^3$ | R$^4$ |
|---|---|---|---|---|
| NO$_2$ | NO$_2$ | CF$_3$ | CBrF$_2$ | NH$_2$ |
| Cl | Cl | CF$_3$ | CBr$_2$F | NH$_2$ |
| NO$_2$ | NO$_2$ | CF$_3$ | CBr$_2$F | NH$_2$ |
| Cl | Cl | CF$_3$ | CCl$_3$ | NH$_2$ |
| NO$_2$ | NO$_2$ | CF$_3$ | CCl$_3$ | NH$_2$ |
| Cl | Cl | CF$_3$ | CBr$_3$ | NH$_2$ |
| NO$_2$ | NO$_2$ | CF$_3$ | CBr$_3$ | NH$_2$ |
| Cl | Cl | CF$_3$ | CF$_2$H | NH$_2$ |
| NO$_2$ | NO$_2$ | CF$_3$ | CF$_2$H | NH$_2$ |
| Cl | Cl | CF$_3$ | CCl$_2$H | NH$_2$ |
| NO$_2$ | NO$_2$ | CF$_3$ | CCl$_2$H | NH$_2$ |
| Cl | Cl | CF$_3$ | CBr$_2$H | NH$_2$ |
| NO$_2$ | NO$_2$ | CF$_3$ | CBr$_2$H | NH$_2$ |
| Cl | Cl | CF$_3$ | CClFH | NH$_2$ |
| NO$_2$ | NO$_2$ | CF$_3$ | CClFH | NH$_2$ |
| Cl | Cl | CF$_3$ | CBrClH | NH$_2$ |
| NO$_2$ | NO$_2$ | CF$_3$ | CBrClH | NH$_2$ |
| Cl | Cl | CF$_3$ | CBrFH | NH$_2$ |

TABLE 4-continued

| X | Y | Z | CR¹R²R³ | R⁴ |
|---|---|---|---|---|
| NO₂ | NO₂ | CF₃ | CBrFH | NH₂ |
| Cl | Cl | CF₃ | CF₂CH₃ | NH₂ |
| NO₂ | NO₂ | CF₃ | CF₂CH₃ | NH₂ |
| Cl | Cl | CF₃ | CF₂CF₂H | NH₂ |
| NO₂ | NO₂ | CF₃ | CF₂CF₂H | NH₂ |

TABLE 5

| X | Y | Z | CR¹R²R³ | R⁴ |
|---|---|---|---|---|
| Cl | Cl | CF₃ | (CF₂)₃H | NH₂ |
| NO₂ | NO₂ | CF₃ | (CF₂)₃H | NH₂ |
| Cl | Cl | CF₃ | CF₂CF₂Cl | NH₂ |
| NO₂ | NO₂ | CF₃ | CF₂CF₂Cl | NH₂ |
| Cl | Cl | CF₃ | CF₂CF₂Br | NH₂ |
| NO₂ | NO₂ | CF₃ | CF₂CF₂Br | NH₂ |
| Cl | Cl | CF₃ | CFClCF₃ | NH₂ |
| NO₂ | NO₂ | CF₃ | CFClCF₃ | NH₂ |
| Cl | Cl | CF₃ | CFBrCF₃ | NH₂ |
| NO₂ | NO₂ | CF₃ | CFBrCF₃ | NH₂ |
| Cl | Cl | CF₃ | CH(CF₃)₂ | NH₂ |
| NO₂ | NO₂ | CF₃ | CH(CF₃)₂ | NH₂ |
| Cl | Cl | CF₃ | CF₂CHFCF₃ | NH₂ |
| NO₂ | NO₂ | CF₃ | CF₂CHFCF₃ | NH₂ |
| Cl | Cl | CF₃ | CF(OCH₃)CF₃ | NH₂ |
| NO₂ | NO₂ | CF₃ | CF(OCH₃)CF₃ | NH₂ |
| Cl | Cl | CF₃ | CF₂CCl₂F | NH₂ |
| NO₂ | NO₂ | CF₃ | CF₂CCl₂F | NH₂ |
| Cl | Cl | CF₃ | CF₂CBr₂F | NH₂ |
| NO₂ | NO₂ | CF₃ | CF₂CBr₂F | NH₂ |
| Cl | Cl | CF₃ | CFClCBrF₂ | NH₂ |
| NO₂ | NO₂ | CF₃ | CFClCBrF₂ | NH₂ |

TABLE 6

| X | Y | Z | CR¹R²R³ | R⁴ |
|---|---|---|---|---|
| Cl | Cl | CF₃ | CF₂CClFCClF₂ | NH₂ |
| NO₂ | NO₂ | CF₃ | CF₂CClFCClF₂ | NH₂ |
| Cl | Cl | CF₃ | CF₂CBrFH | NH₂ |
| NO₂ | NO₂ | CF₃ | CF₂CBrFH | NH₂ |
| Cl | Cl | CF₃ | CF₂CClFH | NH₂ |
| NO₂ | NO₂ | CF₃ | CF₂CClFH | NH₂ |
| Cl | Cl | CF₃ | (CF₂)₄H | NH₂ |
| NO₂ | NO₂ | CF₃ | (CF₂)₄H | NH₂ |
| Cl | Cl | CF₃ | CF₂SCH₃ | NH₂ |
| NO₂ | NO₂ | CF₃ | CF₂SCH₃ | NH₂ |
| Cl | Cl | CF₃ | CF₂S(O)CH₃ | NH₂ |
| NO₂ | NO₂ | CF₃ | CF₂S(O)CH₃ | NH₂ |
| Cl | Cl | CF₃ | CF₂S(O)₂CH₃ | NH₂ |
| NO₂ | NO₂ | CF₃ | CF₂S(O)₂CH₃ | NH₂ |
| Cl | Cl | CF₃ | CF₂SCH₂CH₃ | NH₂ |
| NO₂ | NO₂ | CF₃ | CF₂SCH₂CH₃ | NH₂ |
| Cl | Cl | CF₃ | CF₂SCF₃ | NH₂ |
| NO₂ | NO₂ | CF₃ | CF₂SCF₃ | NH₂ |
| Cl | Cl | CF₃ | CF₂CF(CF₃)₂ | NH₂ |
| NO₂ | NO₂ | CF₃ | CF₂CF(CF₃)₂ | NH₂ |
| Cl | Cl | OCF₃ | CF₃ | NH₂ |
| NO₂ | NO₂ | OCF₃ | CF₃ | NH₂ |
| Cl | Cl | OCF₃ | C₂F₅ | NH₂ |

TABLE 7

| X | Y | Z | CR¹R²R³ | R⁴ |
|---|---|---|---|---|
| NO₂ | NO₂ | OCF₃ | C₂F₅ | NH₂ |
| Cl | Cl | OCF₃ | CClF₂ | NH₂ |
| NO₂ | NO₂ | OCF₃ | CClF₂ | NH₂ |
| Cl | Cl | C₂F₅ | CF₃ | NH₂ |
| NO₂ | NO₂ | C₂F₅ | CF₃ | NH₂ |

TABLE 7-continued

| X | Y | Z | CR¹R²R³ | R⁴ |
|---|---|---|---|---|
| Cl | Cl | C₂F₅ | C₂F₅ | NH₂ |
| NO₂ | NO₂ | C₂F₅ | C₂F₅ | NH₂ |
| Cl | Cl | C₂F₅ | CClF₂ | NH₂ |
| NO₂ | NO₂ | C₂F₅ | CClF₂ | NH₂ |
| Cl | Cl | OC₂F₅ | CF₃ | NH₂ |
| NO₂ | NO₂ | OC₂F₅ | CF₃ | NH₂ |
| Cl | Cl | OC₂F₅ | C₂F₅ | NH₂ |
| NO₂ | NO₂ | OC₂F₅ | C₂F₅ | NH₂ |
| Cl | Cl | OC₂F₅ | CClF₂ | NH₂ |
| NO₂ | NO₂ | OC₂F₅ | CClF₂ | NH₂ |
| Cl | Cl | CF₃ | CF₃ | NHCH₃ |
| NO₂ | NO₂ | CF₃ | CF₃ | NHCH₃ |
| Cl | Cl | CF₃ | C₂F₅ | NHCH₃ |
| NO₂ | NO₂ | CF₃ | C₂F₅ | NHCH₃ |
| Cl | Cl | CF₃ | CClF₂ | NHCH₃ |
| NO₂ | NO₂ | CF₃ | CClF₂ | NHCH₃ |
| Cl | Cl | CF₃ | CF₃ | N(CH₃)₂ |
| NO₂ | NO₂ | CF₃ | CF₃ | N(CH₃)₂ |

TABLE 8

| X | Y | Z | CR¹R²R³ | R⁴ |
|---|---|---|---|---|
| Cl | Cl | CF₃ | C₂F₅ | N(CH₃)₂ |
| NO₂ | NO₂ | CF₃ | C₂F₅ | N(CH₃)₂ |
| Cl | Cl | CF₃ | CClF₂ | N(CH₃)₂ |
| NO₂ | NO₂ | CF₃ | CClF₂ | N(CH₃)₂ |
| Cl | Cl | CF₃ | CF₃ | NHCH₂CH₃ |
| NO₂ | NO₂ | CF₃ | CF₃ | NHCH₂CH₃ |
| Cl | Cl | CF₃ | C₂F₅ | NHCH₂CH₃ |
| NO₂ | NO₂ | CF₃ | C₂F₅ | NHCH₂CH₃ |
| Cl | Cl | CF₃ | CClF₂ | NHCH₂CH₃ |
| NO₂ | NO₂ | CF₃ | CClF₂ | NHCH₂CH₃ |
| Cl | Cl | CF₃ | CF₃ | N(CH₂CH₃)₂ |
| NO₂ | NO₂ | CF₃ | CF₃ | N(CH₂CH₃)₂ |
| Cl | Cl | CF₃ | C₂F₅ | N(CH₂CH₃)₂ |
| NO₂ | NO₂ | CF₃ | C₂F₅ | N(CH₂CH₃)₂ |
| Cl | Cl | CF₃ | CClF₂ | N(CH₂CH₃)₂ |
| NO₂ | NO₂ | CF₃ | CClF₂ | N(CH₂CH₃)₂ |
| Cl | Cl | CF₃ | CF₃ | N(CH₂CH₂CH₃)₂ |
| NO₂ | NO₂ | CF₃ | CF₃ | N(CH₂CH₂CH₃)₂ |
| Cl | Cl | CF₃ | C₂F₅ | N(CH₂CH₂CH₃)₂ |
| NO₂ | NO₂ | CF₃ | C₂F₅ | N(CH₂CH₂CH₃)₂ |
| Cl | Cl | CF₃ | CClF₂ | N(CH₂CH₂CH₃)₂ |
| NO₂ | NO₂ | CF₃ | CClF₂ | N(CH₂CH₂CH₃)₂ |
| Cl | Cl | CF₃ | CF₃ | NHCOCH₃ |

TABLE 9

| X | Y | Z | CR¹R²R³ | R⁴ |
|---|---|---|---|---|
| NO₂ | NO₂ | CF₃ | CF₃ | NHCOCH₃ |
| Cl | Cl | CF₃ | C₂F₅ | NHCOCH₃ |
| NO₂ | NO₂ | CF₃ | C₂F₅ | NHCOCH₃ |
| Cl | Cl | CF₃ | CClF₂ | NHCOCH₃ |
| NO₂ | NO₂ | CF₃ | CClF₂ | NHCOCH₃ |
| Cl | Cl | CF₃ | CF₃ | N(COCH₃)₂ |
| NO₂ | NO₂ | CF₃ | CF₃ | N(COCH₃)₂ |
| Cl | Cl | CF₃ | C₂F₅ | N(COCH₃)₂ |
| NO₂ | NO₂ | CF₃ | C₂F₅ | N(COCH₃)₂ |
| Cl | Cl | CF₃ | CClF₂ | N(COCH₃)₂ |
| NO₂ | NO₂ | CF₃ | CClF₂ | N(COCH₃)₂ |
| Cl | Cl | CF₃ | CF₃ | NHCO₂CH₃ |
| NO₂ | NO₂ | CF₃ | CF₃ | NHCO₂CH₃ |
| Cl | Cl | CF₃ | C₂F₅ | NHCO₂CH₃ |
| NO₂ | NO₂ | CF₃ | C₂F₅ | NHCO₂CH₃ |
| Cl | Cl | CF₃ | CClF₂ | NHCO₂CH₃ |
| NO₂ | NO₂ | CF₃ | CClF₂ | NHCO₂CH₃ |
| Cl | Cl | CF₃ | CF₃ | N(CO₂CH₃)₂ |
| NO₂ | NO₂ | CF₃ | CF₃ | N(CO₂CH₃)₂ |
| Cl | Cl | CF₃ | C₂F₅ | N(CO₂CH₃)₂ |
| NO₂ | NO₂ | CF₃ | C₂F₅ | N(CO₂CH₃)₂ |

TABLE 9-continued

| X | Y | Z | CR$^1$R$^2$R$^3$ | R$^4$ |
|---|---|---|---|---|
| Cl | Cl | CF$_3$ | CClF$_2$ | N(CO$_2$CH$_3$)$_2$ |
| NO$_2$ | NO$_2$ | CF$_3$ | CClF$_2$ | N(CO$_2$CH$_3$)$_2$ |

TABLE 10

| X | Y | Z | CR$^1$R$^2$R$^3$ | R$^4$ |
|---|---|---|---|---|
| Cl | Cl | CF$_3$ | CF$_3$ | NHCH$_2$OCH$_3$ |
| NO$_2$ | NO$_2$ | CF$_3$ | CF$_3$ | NHCH$_2$OCH$_3$ |
| Cl | Cl | CF$_3$ | C$_2$F$_5$ | NHCH$_2$OCH$_3$ |
| NO$_2$ | NO$_2$ | CF$_3$ | C$_2$F$_5$ | NHCH$_2$OCH$_3$ |
| Cl | Cl | CF$_3$ | CClF$_2$ | NHCH$_2$OCH$_3$ |
| NO$_2$ | NO$_2$ | CF$_3$ | CClF$_2$ | NHCH$_2$OCH$_3$ |
| Cl | Cl | CF$_3$ | CF$_3$ | NCH$_3$(COCH$_3$) |
| NO$_2$ | NO$_2$ | CF$_3$ | CF$_3$ | NCH$_3$(COCH$_3$) |
| Cl | Cl | CF$_3$ | C$_2$F$_5$ | NCH$_3$(COCH$_3$) |
| NO$_2$ | NO$_2$ | CF$_3$ | C$_2$F$_5$ | NCH$_3$(COCH$_3$) |
| Cl | Cl | CF$_3$ | CClF$_2$ | NCH$_3$(COCH$_3$) |
| NO$_2$ | NO$_2$ | CF$_3$ | CClF$_2$ | NCH$_3$(COCH$_3$) |
| Cl | Cl | CF$_3$ | CF$_3$ | NCH$_3$(CO$_2$CH$_3$) |
| NO$_2$ | NO$_2$ | CF$_3$ | CF$_3$ | NCH$_3$(CO$_2$CH$_3$) |
| Cl | Cl | CF$_3$ | C$_2$F$_5$ | NCH$_3$(CO$_2$CH$_3$) |
| NO$_2$ | NO$_2$ | CF$_3$ | C$_2$F$_5$ | NCH$_3$(CO$_2$CH$_3$) |
| Cl | Cl | CF$_3$ | CClF$_2$ | NCH$_3$(CO$_2$CH$_3$) |
| NO$_2$ | NO$_2$ | CF$_3$ | CClF$_2$ | NCH$_3$(CO$_2$CH$_3$) |
| Cl | Cl | CF$_3$ | CF$_3$ | NCH$_3$(CH$_2$OCH$_3$) |
| NO$_2$ | NO$_2$ | CF$_3$ | CF$_3$ | NCH$_3$(CH$_2$OCH$_3$) |
| Cl | Cl | CF$_3$ | C$_2$F$_5$ | NCH$_3$(CH$_2$OCH$_3$) |
| NO$_2$ | NO$_2$ | CF$_3$ | C$_2$F$_5$ | NCH$_3$(CH$_2$OCH$_3$) |
| Cl | Cl | CF$_3$ | CClF$_2$ | NCH$_3$(CH$_2$OCH$_3$) |
| NO$_2$ | NO$_2$ | CF$_3$ | CClF$_2$ | NCH$_3$(CH$_2$OCH$_3$) |

TABLE 11

| X | Y | Z | CR$^1$R$^2$R$^3$ | R$^4$ |
|---|---|---|---|---|
| Cl | Cl | CF$_3$ | CF$_3$ | NCOCH$_3$(CO$_2$CH$_3$) |
| NO$_2$ | NO$_2$ | CF$_3$ | CF$_3$ | NCOCH$_3$(CO$_2$CH$_3$) |
| Cl | Cl | CF$_3$ | C$_2$F$_5$ | NCOCH$_3$(CO$_2$CH$_3$) |
| NO$_2$ | NO$_2$ | CF$_3$ | C$_2$F$_5$ | NCOCH$_3$(CO$_2$CH$_3$) |
| Cl | Cl | CF$_3$ | CClF$_2$ | NCOCH$_3$(CO$_2$CH$_3$) |
| NO$_2$ | NO$_2$ | CF$_3$ | CClF$_2$ | NCOCH$_3$(CO$_2$CH$_3$) |
| Cl | Cl | CF$_3$ | CF$_3$ | NCOCH$_3$(CH$_2$OCH$_3$) |
| NO$_2$ | NO$_2$ | CF$_3$ | CF$_3$ | NCOCH$_3$(CH$_2$OCH$_3$) |
| Cl | Cl | CF$_3$ | C$_2$F$_5$ | NCOCH$_3$(CH$_2$OCH$_3$) |
| NO$_2$ | NO$_2$ | CF$_3$ | C$_2$F$_5$ | NCOCH$_3$(CH$_2$OCH$_3$) |
| Cl | Cl | CF$_3$ | CClF$_2$ | NCOCH$_3$(CH$_2$OCH$_3$) |
| NO$_2$ | NO$_2$ | CF$_3$ | CClF$_2$ | NCOCH$_3$(CH$_2$OCH$_3$) |
| Cl | Cl | CF$_3$ | CF$_3$ | NCO$_2$CH$_3$(CH$_2$OCH$_3$) |
| NO$_2$ | NO$_2$ | CF$_3$ | CF$_3$ | NCO$_2$CH$_3$(CH$_2$OCH$_3$) |
| Cl | Cl | CF$_3$ | C$_2$F$_5$ | NCO$_2$CH$_3$(CH$_2$OCH$_3$) |
| NO$_2$ | NO$_2$ | CF$_3$ | C$_2$F$_5$ | NCO$_2$CH$_3$(CH$_2$OCH$_3$) |
| Cl | Cl | CF$_3$ | CClF$_2$ | NCO$_2$CH$_3$(CH$_2$OCH$_3$) |
| NO$_2$ | NO$_2$ | CF$_3$ | CClF$_2$ | NCO$_2$CH$_3$(CH$_2$OCH$_3$) |
| Cl | Cl | CF$_3$ | CF$_3$ | N=CH(OCH$_3$) |
| NO$_2$ | NO$_2$ | CF$_3$ | CF$_3$ | N=CH(OCH$_3$) |
| Cl | Cl | CF$_3$ | C$_2$F$_5$ | N=CH(OCH$_3$) |
| NO$_2$ | NO$_2$ | CF$_3$ | C$_2$F$_5$ | N=CH(OCH$_3$) |
| Cl | Cl | CF$_3$ | CClF$_2$ | N=CH(OCH$_3$) |
| NO$_2$ | NO$_2$ | CF$_3$ | CClF$_2$ | N=CH(OCH$_3$) |

TABLE 12

| X | Y | Z | CR$^1$R$^2$R$^3$ | R$^4$ |
|---|---|---|---|---|
| Cl | Cl | CF$_3$ | CF$_3$ | N=CCH$_3$(OCH$_3$) |
| NO$_2$ | NO$_2$ | CF$_3$ | CF$_3$ | N=CCH$_3$(OCH$_3$) |
| Cl | Cl | CF$_3$ | C$_2$F$_5$ | N=CCH$_3$(OCH$_3$) |
| NO$_2$ | NO$_2$ | CF$_3$ | C$_2$F$_5$ | N=CCH$_3$(OCH$_3$) |
| Cl | Cl | CF$_3$ | CClF$_2$ | N=CCH$_3$(OCH$_3$) |
| NO$_2$ | NO$_2$ | CF$_3$ | CClF$_2$ | N=CCH$_3$(OCH$_3$) |
| Cl | Cl | CF$_3$ | CF$_3$ | N=CHCH$_3$ |
| NO$_2$ | NO$_2$ | CF$_3$ | CF$_3$ | N=CHCH$_3$ |
| Cl | Cl | CF$_3$ | C$_2$F$_5$ | N=CHCH$_3$ |
| NO$_2$ | NO$_2$ | CF$_3$ | C$_2$F$_5$ | N=CHCH$_3$ |
| Cl | Cl | CF$_3$ | CClF$_2$ | N=CHCH$_3$ |
| NO$_2$ | NO$_2$ | CF$_3$ | CClF$_2$ | N=CHCH$_3$ |
| Cl | Cl | CF$_3$ | CF$_3$ | N=C(CH$_3$)$_2$ |
| NO$_2$ | NO$_2$ | CF$_3$ | CF$_3$ | N=C(CH$_3$)$_2$ |
| Cl | Cl | CF$_3$ | C$_2$F$_5$ | N=C(CH$_3$)$_2$ |
| NO$_2$ | NO$_2$ | CF$_3$ | C$_2$F$_5$ | N=C(CH$_3$)$_2$ |
| Cl | Cl | CF$_3$ | CClF$_2$ | N=C(CH$_3$)$_2$ |
| NO$_2$ | NO$_2$ | CF$_3$ | CClF$_2$ | N=C(CH$_3$)$_2$ |
| Cl | Cl | CF$_3$ | CF$_3$ | N=CHN(CH$_3$)$_2$ |
| NO$_2$ | NO$_2$ | CF$_3$ | CF$_3$ | N=CHN(CH$_3$)$_2$ |
| Cl | Cl | CF$_3$ | C$_2$F$_5$ | N=CHN(CH$_3$)$_2$ |
| NO$_2$ | NO$_2$ | CF$_3$ | C$_2$F$_5$ | N=CHN(CH$_3$)$_2$ |
| Cl | Cl | CF$_3$ | CClF$_2$ | N=CHN(CH$_3$)$_2$ |
| NO$_2$ | NO$_2$ | CF$_3$ | CClF$_2$ | N=CHN(CH$_3$)$_2$ |

TABLE 13

| X | Y | Z | CR$^1$R$^2$R$^3$ | R$^4$ |
|---|---|---|---|---|
| Cl | Cl | CF$_3$ | CF$_3$ | N=CCH$_3$[N(CH$_3$)$_2$] |
| NO$_2$ | NO$_2$ | CF$_3$ | CF$_3$ | N=CCH$_3$[N(CH$_3$)$_2$] |
| Cl | Cl | CF$_3$ | C$_2$F$_5$ | N=CCH$_3$[N(CH$_3$)$_2$] |
| NO$_2$ | NO$_2$ | CF$_3$ | C$_2$F$_5$ | N=CCH$_3$[N(CH$_3$)$_2$] |
| Cl | Cl | CF$_3$ | CClF$_2$ | N=CCH$_3$[N(CH$_3$)$_2$] |
| NO$_2$ | NO$_2$ | CF$_3$ | CClF$_2$ | N=CCH$_3$[N(CH$_3$)$_2$] |

The present compounds can exhibit controlling activity against pests including harmful arthropods (e.g., harmful insects and acarines) and harmful nematodes. Specific examples of the pests are as follows:

Isopoda:

*Oniscus asellus, Armadillidium vulgare, Porcellio scaber*, etc.;

Diplopoda:

*Blanilus guttulatus* etc.;

Chilopoda:

*Geophilus carpophagus*, Scutigera spp., *Scolopendra suhspinipes*, Thereunema spp., etc.;

Symphyla:

*Scutigerella immaculata* etc.;

Thysanura:

*Ctenolepisma villosa, Lepisma saccharina*, etc.;

Psocoptera:

*Trogium pulsatorium* etc.;

Collembola:

*Onychiurus armatus* etc.;

Isoptera:

Mastotermitidae; Termopsidae such as Zootermopsis, Archotermopsis, Hodotermopsis (e.g., *Hodotermopsis japonica*), and Porotetmes; Kalotermitidae such as Kalotermes, Neotermes (e.g., *Neotermes koshuensis*), Cryptotermes (e.g., *Cryptotermes domesticus*), Incisitermes (e.g., *Incisitermes minor*), and Glyptotermes (e.g., *Glyptotermes satsumaensis, G. nakajimai, G. fuscus*); Hodotermitidae such as Hodotermes, Microhodotermes, and Anacanthotermes; Rhinotermitidae such as Reticulitermes (e.g, *Retitulitermes speratus*, R. sp, *R. flaviceps, R. miyatakei*), Heterotermes, Coptotermes (e.g., *Coptotermes*

*formosanus*), and Schedolinotermes; Serritermitidae; Termitidae such as Amitermes, Drepanotermes, Hopitalitermes, Trinervitermes, Macrotermes, Odontotermes (e.g., *Odontotermes formosanus*), Microtermes, Nasutitermes (*Nasutitermes takasagoensis*), Pericapritermes (e.g., *Pericapritermes nitobei*), and Anoplotermes, etc.;

Dictyoptera:

*Blatta orientalis, Periplaneta americana, P. fuliginosa, Leucophaea maderae, Blattella germanica*, etc.;

Orthoptera:

Gryllotalpa spp., *Acheta domesticus, Teleogryllus emma, Locusta migratoria, Melanoplus differentialis, Schistocerca gregaria*, etc.;

Dermaptera:

*Labidura riparia, Forficula auricularia*, etc.;

Anoplura:

*Phthirus pubis, Pediculus humanus, Haematopinus suls, Haematopinus eurysternus, Damalinia ovis*, Linognathus spp., Solenopotes spp., etc.;

Mallophaga:

Trichodectes spp., Tromenopon spp., Bovicola spp., Felicola spp., etc.;

Thysanoptera:

*Frankliniella intonsa, Thrips tabaci, T. palmi*, etc.;

Heteroptera:

Nezara spp., Eurygaster spp., *Dysdercus intermedius, Cimex lectularius*, Triatoma spp., *Rhodnius prolixus, Nezara antennata, Cletus punetiger*, etc.;

Homoptera:

*Aleurocanthus spiniferus, Bemisia tabaci, Trialeurodes vaporariorum, Aphis gossypii, Brevocoryne brassicae, Cryptomyzus ribis, Aphis fabae, Macrosiphum euphorbiae, Myzus persicae, Phorodon humuli*, Empoasca spp., *Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp., *Phylloxera vastatrix*, etc.;

Lepidoptera:

*Pectinophora gossypiella, Lithocolletis blancardella, Plutella xylostella, Malacosoma neustria, Euproctis subflava, Lymantria dispar, Bucculatrix pyrivorella, Phyllocnistis citrella*, Agrotis spp., Euxoa spp., *Earias insulana*, Heliothis spp., *Spodoptera exigua, S. litura*, Spodoptera spp., *Mamestra brassicae, Trichoplusia ni, Carpocapsa pomonella*, Pieris spp., Chilo spp., *Pyrausta nubilalis, Ephestia kuehniella, Galleria mellonella, Tineola bisselliella, Tenea translucens, Homona magnanima, Tortrix viridana*, etc.;

Coleoptera:

*Anobium punctatum, Rhizopertha dominica, Acanthoscelides obtectus, Agelastica alni, Leptinotarsa decemlineata, Phaedon cochleariae*, Diabrotica spp., *Psylliodes angusticollis, Phyllotreta striolata*, Epilachna spp., Atomaria spp., *Oryzaephilus surinamensis*, Anthonomus spp., Sitophilus spp., *Otiorhynchus sulcatus, Cosmopolites sordidus, Ceuthorhyncidius albosuturalis, Hypera postica*, Dermestes spp., Trogoderma spp., *Attagenus unicolor*; Lyctridae such as *Lyctus dentatum, L. planicollis, L. sinensis, L. linearis, L. brunneus*, and *L. africanus; Meligethes aeneus*, Ptinus spp., *Gibbium psylloides*, Tribolium spp., *Tenebrio molitor*, Agriotes spp., *Melolontha mololontha*; Scolytidae such as Xyleborus and Scolytoplatypus; Cerambycidae such as Monochamus, Hylotrupes, Hesperophanus, Chlorophorus, Palaeocallidium, Semanotus, Purpuricenus, and Stromatium; Platypodidae such as Crossotarsus and Platypus; Bostrychidae such as Dinoderus, Bostrychus, and Sinoderus; Anobiidae such as Ernobius, Anobium, Xyletinus, Xestobium, Ptilinus, Nicobium, and Ptilineurus; Buprestidae, etc.;

Hymenoptera:

Diprion spp., Hoplocampa spp., Lasius spp., *Formica japonica*, Vespa spp.; Siricidae such as Urocerus and Sirex, etc.;

Diptera:

Aedes spp., Anopheles spp., Culex spp., *Drosophila melanogaster, Musca domestica*, Fannia spp., Calliphora spp., Lucilia spp., Chrysomya spp., Cuterebra spp., Gastrophilus spp., Stomoxys spp., Oestrus spp., Hypoderma spp., Tabanus spp., *Bibio hortulanus, Pegomyia hyoscyami, Ceratitis capitata, Dacus dorsalis, Tipula paludosa*, Simulium spp., Eusimulium spp., Phlebotomus spp., Culicoides spp., Chrysops spp., Haematopota spp., Braula spp., Morellia spp., Glossina spp., Wohlfahrtia spp., Sarcophaga spp., Lipoptena spp., Melophagus spp., Muscina spp., etc.;

Siphonaptera:

*Xenopsylla cheopis, Ctenocephalides felis, Ctenocephalides canis*, Ceratophyllus spp., Pulex spp., etc.;

Arachnida:

*Scorpio maurus, Latrodectus mactans*, Chiracanthium spp., etc.;

Acarina:

Otodectes spp., *Acarus siro*, Argas spp., Ornithodoros spp., Ornithonyssus spp., Dermanyssus spp., Eriophyes spp., *Haemaphyxalis longicornis, Boophilus microplus*, Rhipicephalus spp., *Chelacaropsis moorei*, Dermatophagoides spp., Hyalomma spp., *Ixodes ovatus, Ixodes persulcatus, Psoroptes equi*, Chorioptes spp., Sarcoptes spp., Tarsonemus spp., *Bryobia praetiosa*, Panonychus spp., Tetranychus spp., Dermacentor spp., Haemaphysalis spp., Raillietia spp., Pneumonyssus spp., Sternostorma spp., Acarapis spp., Cheyletiella spp., Myobia spp., Psorergates spp., Demodex spp., Trombicula spp., Listrophorus spp., Tyrophagus spp., Sarcoptes spp., Notoedres spp., Cytodides spp., Laminosioptes spp., etc.;

Plant parasitic nematodes:

Pratylenchus spp., Grobodera spp., Heterodera spp., Meloidogyne spp., Aphelenchoides spp., Notylenchus spp., *Bursaphelenchus lignicolus*, etc.

The present compounds can also be used for the effective control of pests having improved resistance to the conventional pesticides.

When the present compounds are used as the active ingredients of pesticides, they may be used as such or in the form of salts (agrochemically acceptable salts with inorganic acids such as hydrochloric acid and sulfuric acid or organic acids such as p-toluenesulfonic acid) without addition of any other ingredients. However, the present compounds are usually mixed with solid carriers, liquid carriers, gaseous carriers or baits, or absorbed in base materials such as porous ceramic plates or nonwoven fabrics, followed by addition of surfactants and other auxiliaries, if necessary, and they are then formulated into various forms, such as oil sprays, emulsifiable concentrates, wettable powders, flowables, granules, dusts, aerosols, fumigants (e.g., foggings), vaporizable formulations, smoking formulations, poison baits, anti-acarine sheets, or resin formulations.

Each of these formulations may usually contain at least one of the present compounds as an active ingredient in an amount of 0.01% to 95% by weight.

The solid carrier which can be used in the formulation may include fine powder or granules of clay materials such as kaolin clay, diatomaceous earth, synthetic hydrated silicon oxide, bentonite, Fubasami clay, and acid clay; various kinds of talc, ceramics, and other inorganic minerals such as sericite, quartz, sulfur, activated carbon, calcium carbonate, and hydrated silica; and chemical fertilizers such as ammonium sulfate, ammonium phosphate, ammonium nitrate, urea, and ammonium chloride.

The liquid carrier may include water; alcohols such as methanol and ethanol; ketones such as acetone and methyl ethyl ketone; aromatic hydrocarbons such as benzene, toluene, xylene, ethylbenzene, and methylnaphthalene; aliphatic hydrocarbons such as hexane, cyclohexane, kerosene, and light oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane, and carbon tetrachloride; dimethyl sulfoxide; and vegetable oils such as soybean oil and cottonseed oil.

The gaseous carrier or propellant may include Freon gas, butane gas, LPG (liquefied petroleum gas), dimethyl ether, and carbon dioxide.

The base material for used in poison baits may include bait materials such as grain powder, vegetable oils, sugars, and crystalline cellulose; antioxidants such as dibutylhydroxytoluene and nordihydroguaiaretic acid; preservatives such as dehydroacetic acid; substances for preventing erroneous eating, such as red pepper powder; and attractant flavors such as cheese flavor and onion flavor.

The surfactant may include alkyl sulfates, alkyl sulfonates, alkyl arylsulfonates, alkyl aryl ethers and their polyoxyethylene derivatives, polyethylene glycol ethers, polyhydric alcohol esters, and sugar alcohol derivatives.

The auxiliaries such as adhesive agents or dispersants may include casein, gelatin; polysaccharides such as starch, gum arabic, cellulose derivatives, and alginic acid; lignin derivatives, bentonite, sugars, and synthetic water-soluble polymers such as polyvinyl alcohol, polyvinyl pyrrolidone, and polyacrylic acid.

The stabilizing agent may include PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids and their esters.

When the present compounds are used as insecticides, acaricides, or nematocides for agriculture, the amounts for their application are usually in the range of 0.1 to 100 g per 10 ares. For emulsifiable concentrates, wettable powders, flowables, and other similar formulations to be used after dilution with water, the concentrations for their application usually in the range of 1 to 10,000 ppm. The application of granules, dusts, or other similar formulations is carried out as such formulations without dilution. When the present compounds are used as insecticides, acaricides, or nematocides for epidemic prevention, they are applied after dilution with water to concentrations of 0.1 to 500 ppm in the case of emulsifiable concentrates, wettable powders, flowable, or other similar formulations, or they are applied as such in the case of oil sprays, aerosols, fumigants, poisonous baits, anti-acarine sheets, or other similar formulations. These application amounts or concentrations may vary depending upon types of formulations, times, places, and methods of application, kinds of pests, degree of damage, and other factors; they can therefore be increased or decreased without limitation to the above ranges.

When the present compositions are used as insecticides or acaricides for the control of ectoparasites on domestic animals such as cattle and pigs or pets such as cats and dogs, they or their salts may be applied by the known veterinary methods, for example, tablets, capsules, immersion solutions, boli, feed incorporation, suppositories, or injection (e.g., intramuscular, subcutaneous, intravenous, intraperitoneal) for systemic control; or spray, pour-on or spot-on treatment with oily or aqueous solutions, or using articles formed from resin formulations into appropriate shapes such as collars and ear tags for non-systemic control. In these cases, the present compounds are usually applied in their own amounts of 0.01 mg to 100 mg per kg of a host animal.

The present compounds can be used in admixture with, or separately but simultaneously with, other insecticides, nematocides, acaricides, bactericides, fungicides, herbicides, plant growth regulators, synergists, fertilizers, soil conditioners and/or animal feeds.

The insecticide, nematocide and/or acaricide which can be used may include organophosphorus compounds such as Fenitrothion [O,O-dimethyl O-(3-methyl-4-nitrophenyl) phosphorothioate], Fenthion [O,O-dimethyl O-(3-methyl-4-(methylthio)phenyl) phophorothioate], Diazinon [O,O-diethyl O-(2-isopropyl-6-methylpyrimidin-4-yl) phosphorothioate], Chlorpyriphos [O,O-diethyl O-(3,5,6-trichloro-2-pyridyl) phosphorothioate], Acephate [O,S-dimethyl acetylphosphoramidothioate], Methidathion [S-((2,3-dihydro-5-methoxy-2-oxo-1,3,4-thiadiazol-3-yl) methyl) O,O-dimethyl phosphorodithioate], Disulfoton [O,O-diethyl S-(2-(ethylthio)ethyl) phosphorothioate], DDVP [2,2-dichlorovinyl dimethyl phosphate], Sulprofos [O-ethyl O-(4-(methylthio)phenyl) S-propyl phosphorodithioate], Cyanophos [O-(4-cyanophenyl) O,O-dimethyl phosphorothioate], Dioxabenzofos [2-methoxy-4H-1,3,2-benzodioxaphosphorin-2-sulfide], Dimethoate [O,O-dimethyl S-(N-methylcarbamoylmethyl) dithiophosphate], Phenthoate [ethyl 2-((dimethoxyphosphinothioyl)thio)phenylacetate], Malathion [diethyl ((dimethoxyphosphinothioyl)thio)-succinate], Trichlorfon [dimethyl (2,2,2-trichloro-1-hydroxyethyl)phosphonate], Azinphos-methyl [S-((3,4-dihydro-4-oxo-1,2,3-benzotriazin-3-yl)methyl) O,O-dimethyl phosphorodithioate], Monocrotophos [dimethyl (E)-1-methyl-2-(methylcarbamoyl)vinyl phosphate], and Ethion [O,O,O',O'-tetraethyl S,S'-methylene bis (phosphorodithioate)]; carbamate compounds such as BPMC [2-sec-butylphenyl methylcarbamate], Benfuracarb [ethyl N-(((((2,3-dihydro-2,2-dimethylbenzofuran-7-yl) oxy)carbonyl)methylamino)thio)-N-isopropyl-β-alaninate], Propoxur [2-isopropoxyphenyl N-methylcarbamate], Carbosulfan [2, 3-dihydro-2,2-dimethyl-7-benzo [b]furanyl N-dibutylaminothio-N-methylcarbamate], Carbaryl [1-naphthyl N-methylcarbamate], Methomyl [S-methyl N-((methylcarbamoyl)oxy)thioacetimidate], Ethiofencarb [2-((ethylthio)methyl)phenyl methylcarbamate], Aldicarb [2-methyl-2-(methylthio)propionaldehyde O-(methylcarbamoyl)oxime], Oxamyl [N,N-dimethyl-2-((methylcarbamoyl)oxy)imino-2-(methylthio)acetamide], and Fenothiocarb [S-(4-phenoxybutyl) N,N-dimethylthiocarbamate]; pyrethroid compounds such as Etofenprox [2-(4-ethoxyphenyl)-2-methylpropyl 3-phenoxybenzyl ether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenprop athrin [(RS)-α-cyano-3-phenoxybenzyl 2,2,3,3-tetramethylcyclopropanecarboxylate], Cypermethrin [(RS)-α-cyano-3-phenoxybenzyl (1RS)-cis,trans-3-(2,2-dichlorovinyl)-2,2-dimethylcyclopropanecarboxylate], Permethrin [3-phenoxybenzyl (1RS)-cis,trans-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], Deltamethrin [(S)-α-cyano-3-phenoxybenzyl (1R)-cis-3-(2,2-dibromovinyl)-2,2-dimethyl cyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α,α,α-trifluoro-p-tolyl)-D-valinate], Bifenthrin [(2-methylbiphenyl-3-yl)methyl (Z)-(1RS)-cis-3-(2-chloro-3,3,3-trifluoro-1-propenyl)-2,2-dimethylcyclopropanecarboxylate], 2-methyl-2-(4-(bromodifluoromethoxy)phenyl)propyl (3-phenoxybenzyl) ether, Tralomethrin [(S)-α-cyano-3-phenoxylbenzyl (1R)-cis-3-(1, 2,2,2-tetrabromoethyl)-2,2-dimethylcyclopropanecarboxylate], Silafluofen [(4-ethoxyphenyl) (3-(4-fluoro-3-phenoxyphenyl)propyl) dimethylsilane], d-Phenothrin [3-phenoxybenzyl (1R-cis,trans)-chrysantemate], Cyphenothrin [(RS)-α-cyano-3-phenoxybenzyl (1R-cis,trans)-chrysantemate], d-Resmethrin [(5-benzyl-3-furyl)methyl (1R-cis,trans)-chrysantemate], Acrinathrin [(S)-α-cyano-3-phenoxybenzyl (1R-cis(Z))-(2,2-dimethyl-3-(3-oxo-3-(1, 1,1,3,3,3-hexafluoropropyloxy)propenyl)cyclopropanecarboxylate], Cyfluthrin [(RS)-α-cyano-4-fluoro-3-phenoxybenzyl 3-(2,2-dichlorovinyl)-2,2-dimethylcyclopropanecarboxylate], Tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], Transfluthrin [2,3,5,6-tetrafluorobenzyl (1R-trans)-3-(2,2-dichlorovinyl)-2,2-dimethylcyclopropanecarboxylate], Tetramethrin [3,4,5,6-tetrahydrophthalimidemethyl (1RS)-cis,trans-chrysantemate], Allethrin [(RS)-3-allyl-2-methyl-4-oxocyclopent-2-enyl (1RS)-cis,trans-chrysantemate], Prallethrin [(S)-2-methyl-4-oxo-3-(2-propynyl)cyclopent-2-enyl (1R)-cis,trans-chrysantemate], Empenthrin [(RS)-1-ethynyl-2-methyl-2-pentenyl (1R)-cis,trans-chrysantemate], Imiprothrin [2,5-dioxo-3-(prop-2-ynyl)imidazolidin-1-ylmethyl (1R)-cis,trans-2,2-dimethyl-3-(2-methyl-1-propenyl)cyclopropanecarboxylate], d-Furamethrin [5-(2-propynyl)furfuryl (1R)-cis,trans-chrysantemate], and 5-(2-propynyl)furfuryl 2,2,3,3-tetramethylcyclopropanecarboxylate; thiadiazine derivatives such as Buprofezin [2-tert-butylimino-3-isopropyl-5-phenyl-1,3,5-thiadiazin-4-one]; nitroimidazolidine derivatives; Nereistoxin derivatives such as Cartap [S,S'-(2-(dimethylamino)trimethylene) bis(thiocarbamate)], Thiocyclam [N,N-dimethyl-1,2,3-trithian-5-ylamine], and Bensultap [S,S'-(2-(dimethylamino)-trimethylene) di(benzenethiosulfonate)]; N-cyanoamidine derivatives such as N-cyano-N'-methyl-N'-(6-chloro-3-pyridylmethyl) acetamidine; chlorinated hydrocarbon compounds such as Endosulfan [6,7,8,9,10,10-hexachloro-1,5,5a, 6,9,9a-hexahydro-6,9-methano-2,4,3-benzodioxathiepin oxide], γ-BHC [1,2,3,4,5,6-hexachlorocyclohexane], and 1,1-bis(p-chlorophenyl)-2,2,2-trichloroethanol; benzoylphenylurea compounds such as Chlorfluazuron [1-(3,5-dichloro-4-((3-chloro-5-(trifluoromethyl)pyridin-2-yl)oxy)phenyl)-3-(2,6-difluorobenzoyl)urea], Teflubenzuron [1-(3,5-dichloro-2,4-difluorophenyl)-3-(2,6-difluorobenzoyl)urea], and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-((methylimino) dimethylidine)-di-2,4-xylidine], and Chlordimeform [N'-(4-chloro-2-methylphenyl)-N,N-dimethylmethanimidamide]; thiourea derivatives such as Diafenthiuron [N-(2,6-diisopropyl-4-phenoxyphenyl)-N'-tert-butylcarbodiimide]; phenylpyrazole compounds, Metoxadiazone [5-methoxy-3-(2-methoxyphenyl)-1,3,4-oxadiazol-2(3H)-one], Bromopropylate [isopropyl 4,4'-dibromobenzylate], Tetradifon [4-chlorophenyl 2,4,5-trichlorophenylsulfone], Quinomethionate [S,S-(6-methylquinoxalin-2,3-diyl) dithiocarbonate], Propargite [2-(4-tert-butylphenoxy) cyclohexyl prop-2-yl sulfite], Fenbutatin oxide [bis(tris(2-methyl-2-phenylpropyl)tin)oxide], Hexythiazox [(4RS, 5RS)-5-(4-chlorophenyl)-N-chlorohexyl-4-methyl-2-oxo-1, 3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyridazin-3(2H)-one], Fenpyroximate [tert-butyl (E)-4-(((((1,3-dimethyl-5-phenoxypyrazol-4-yl)methylene)amino)oxy)methyl) benzoate], Tebfenpyrad [N-(4-tert-butylbenzyl)-4-chloro-3-ethyl-1-methyl-5-pyrazolecarboxamide], polynactin complexes [e.g., tetranactin, dinactin, trinactin], Pyrimidifen [5-chloro-N-(2-(4-(2-ethoxyethyl)-2,3-dimethylphenoxy) ethyl)-6 -ethylpyrimidin-4-amine], Milbemectin, Avermectin, Ivermectin, and Azadilactin [AZAD].

EXAMPLES

The present invention will hereinafter be further illustrated by some production examples, formulation examples, and test examples; however, the present invention is not limited to these examples.

First, production examples for the present compounds and reference production examples for their production intermediates are explained.

Production Example 1

To a mixture of 2.0 g (8.2 mmol) of 3-chloro-4-fluoro-5-nitrobenzotrifluoride, 0.92 g (8.2 mmol) of trifluoroacetamidine, and 16 ml of dimethylsulfoxide was added 0.34 g (8.6 mmol) of sodium hydride (about 60% in oil) under ice cooling, and the mixture was then stirred at room temperature for 2 hours. Water was poured into the reaction mixture, which was extracted with ethyl acetate. The organic layer was washed with saturated aqueous sodium chloride solution, dried over anhydrous magnesium sulfate, and then concentrated under reduced pressure. The residue was subjected to silica gel column chromatography to give 1.5 g of N-(2-chloro-6-nitro-4-trifluoromethylphenyl)-2,2,2-trifluoroacetamidine (hereinafter referred to as present compound 1).

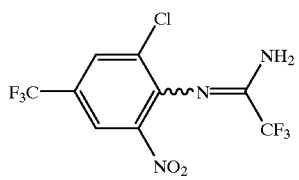

¹H-NMR (300 MHz, CDCl₃/TMS): δ (ppm)=8.15 (s, 1H), 7.92 (d, J=1.6 Hz, 1H), 5.20 (br s, 2H)

Compounds obtained in the same manner as described in Production Example 1 and their NMR data are shown below.

N-(2,6-Difluoro-4-trifluoromethylphenyl)-2,2,2-trifluoroacetamidine (hereinafter referred to as present compound 2)

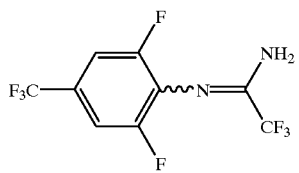

¹H-NMR (300 MHz, CDCl₃/TMS): δ (ppm)=7.24 (s, 2H), 5.15 (br s, 2H)

N-(2,6-Dichloro-4-trifluoromethylphenyl)-2,2,2-trifluoroacetamidine (hereinafter referred to as present compound 3)

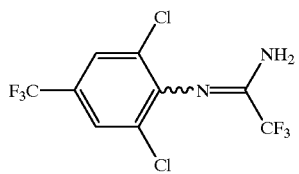

¹H-NMR (250 MHz, CDC₃/TMS): δ (ppm)=7.61 (s, 2H), 5.00 (br s, 2H)

Production Example 2

To a mixture of 40 ml of ethanol and 10 ml of 28% aqueous ammonia was added 3.9 g (10.0 mmol) of N-(2,6-dichloro-4-trifluoromethylphenyl)-2,2,3,3,3-pentafluoropropionimidoyl chloride, and the mixture was stirred at room temperature for 30 minutes. The reaction mixture was concentrated, and water was poured into the residue, which was then extracted with ethyl acetate. The organic layer was dried over anhydrous magnesium sulfate and then concentrated under reduced pressure to give 3.70 g of N-(2,6-dichloro-4-trifluoromethylphenyl)-2,2,3,3,3-pentafluoropropionamidine (hereinafter referred to as present compound 4).

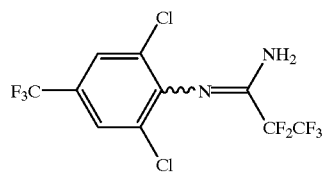

¹H-NMR (300 MHz, CDCl₃/TMS): δ (ppm)=7.61 (s, 2H), 5.09 (br s, 2H)

Compounds obtained in the same manner as described in Production Example 2 and their NMR data are shown below.

2-Chloro-N-(2,6-dichloro-4-trifluoromethylphenyl)-2,2-difluoroacetamidine (hereinafter referred to as present compound 5)

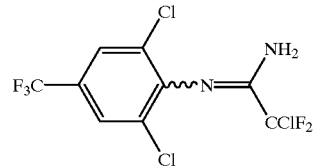

¹H-NMR (300 MHz, CDCl₃/TMS): δ (ppm)=7.61 (s, 2H), 4.97 (br s, 2H)

N-(2,6-Dinitro-4-trifluoromethylphenyl)-2,2,3,3,3-pentafluoropropionamidine (hereinafter referred to as present compound 6)

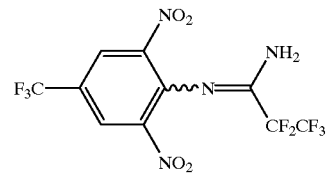

¹H-NMR (250 MHz, CDCl₃/TMS): δ (ppm)=8.41 (s, 2H), 5.53 (br s, 2H)

N-(2, 6-Dichloro-4-trifluoromethylphenyl)-2,2-difluoroacetamidine (hereinafter referred to as present compound 7)

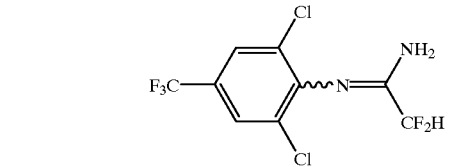

¹H-NMR (300 MHz, CDCl₃/TMS): δ (ppm)=7.60 (s, 2H), 6.24 (t, J=54.4 Hz, 1H), 4.90 (br s, 2H)

N-(2-Chloro-6-nitro-4-trifluoromethylphenyl)-2,2,3,3,3-pentafluoropropionamidine (hereinafter referred to as present compound 8)

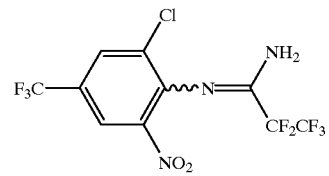

¹H-NMR (300 MHz, CDCl₃/TMS): δ (ppm)=8.15 (d, J=1.4 Hz, 1H), 7.92 (d, J=1.6 Hz, 1H), 5.24 (br s, 2H)

N-(2,6-Difluoro-4-trifluoromethylphenyl)-2,2,3,3,3-pentafluoropropionamidine (hereinafter referred to as present compound 9)

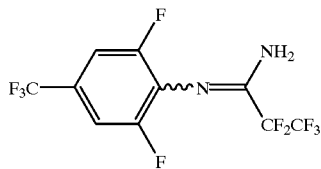

¹H-NMR (300 MHz, CDCl₃/TMS): δ (ppm)=7.24 (s, 2H), 5.20 (br s, 2H)

N-(2-Bromo-6-chloro-4-trifluoromethylphenyl)-2,2,3,3,3-pentafluoropropionamidine (hereinafter referred to as present compound 10)

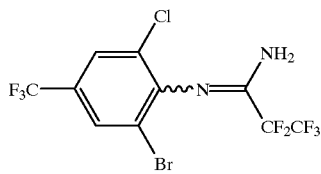

¹H-NMR (300 MHz, CDCl₃/TMS): δ (ppm)=7.78 (s, 1H), 7.66 (s, 1H), 5.06 (br s, 2H)

N-(2,6-Dichloro-4-trifluoromethylphenyl)-2,2,3,3,4,4,4-heptafluorobutyramidine (hereinafter referred to as present compound 11)

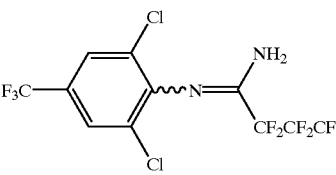

¹H-NMR (300 MHz, CDCl₃/TMS): δ (ppm)=7.62 (s, 2H), 5.06 (br s, 2H)

2,2-Dichloro-N-(2,6-dichloro-4-trifluoromethylphenyl)acetamidine (hereinafter referred to as present compound 12)

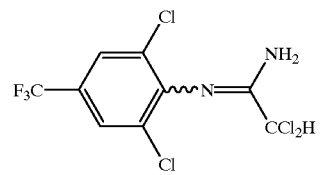

¹H-NMR (250 MHz, CDCl₃/TMS): δ (ppm)=7.59 (s, 2H), 6.33 (s, 1H), 4.96 (br s, 2H)

N-(2-Chloro-6-fluoro-4-trifluoromethylphenyl)-2,2,2-trifluoroacetamidine (hereinafter referred to as present compound 13)

¹H-NMR (300 MHz, CDCl₃/TMS): δ (ppm)=7.53 (s, 1H), 7.33 (d, J=9.1 Hz, 1H), 5.06 (br s, 2H)

N-(2-Chloro-6-cyano-4-trifluoromethylphenyl)-2,2,3,3,3-pentafluoropropionamidine (hereinafter referred to as present compound 14)

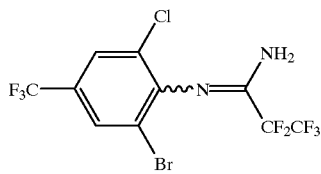

¹H-NMR (300 MHz, CDCl₃/TMS): δ (ppm)=8.15 (d, J=1.8 Hz, 1H), 8.04 (s, 1H), 6.21 (br s, 2H)

N-(2-Chloro-6-methyl-4-trifluoromethylphenyl)-2,2,3,3,3-pentafluoropropionamidine (hereinafter referred to as present compound 15)

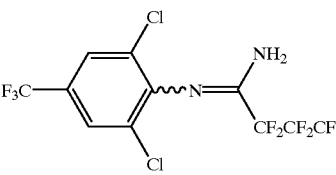

¹H-NMR (250 MHz, CDCl₃/TMS): δ (ppm)=7.53 (s, 1H), 7.38 (s, 1H), 4.96 (br s, 2H), 2.19 (s, 3H)

N-(2,6-Dibromo-4-trifluoromethoxyphenyl)-2,2,3,3,3-pentafluoropropionamidine (hereinafter referred to as present compound 16)

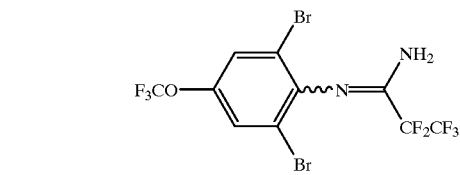

¹H-NMR (250 MHz, CDCl₃/TMS): δ (ppm)=7.48 (s, 2H), 5.11 (br s, 2H)

N-(2,6-Dibromo-4-trifluoromethylphenyl)-2,2,3,3,3-pentafluoropropionamidine (hereinafter referred to as present compound 17)

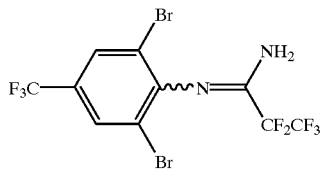

¹H-NMR (250 MHz, CDCl₃/TMS): δ (ppm)=7.82 (s, 2H), 5.06 (br s, 2H)

N-(2,6-Dichloro-4-trifluoromethoxyphenyl)-2,2,3,3,3-pentafluoropropionamidine (hereinafter referred to as present compound 18)

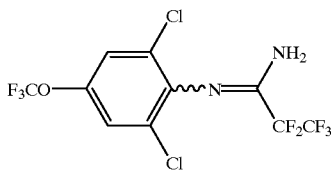

¹H-NMR (250 MHz, CDCl₃/TMS): δ (ppm)=7.27 (s, 2H), 5.06 (br s, 2H)

N-(2-Chloro-6-fluoro-4-trifluoromethylphenyl)-2,2,3,3,3-pentafluoropropionamidine (hereinafter referred to as present compound 19)

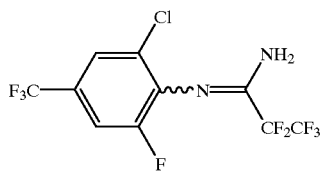

¹H-NMR (300 MHz, CDCl₃/TMS): δ (pm)=7.53 (s, 1H), 7.33 (d, J=9.2 Hz, 1H), 5.14 (br s, 2H)

N-(2,6-Dichloro-4-trifluoromethylphenyl)-2,2,3,3-tetrafluoropropionamidine (hereinafter referred to as present compound 20)

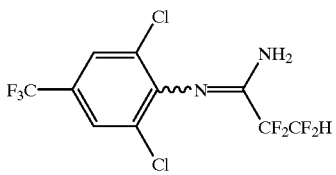

¹H-NMR (250 MHz, CDCl₃/TMS): δ (ppm)=7.61 (s, 2H), 6.41 (tt, J=52.9 Hz, J=5.9 Hz, 1H), 5.13 (br s, 2H)

N-(2,6-Dinitro-4-trifluoromethylphenyl)-2,2,3,3,4,4,4-heptafluorobutyramidine (hereinafter referred to as present compound 21)

¹H-NMR (250 MHz, CDCl₃/TMS): δ (ppm)=8.39 (s, 2H), 5.69 (br s, 2H)

N-(2,6-Dinitro-4-trifluoromethylphenyl)-2,2,2-trichloroacetamidine (hereinafter referred to as present compound 22)

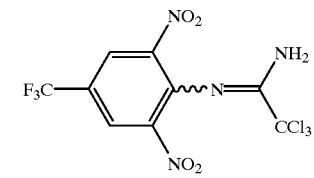

¹H-NMR (250 MHz, CDCl₃/TMS): δ (ppm)=8.41 (s, 2H), 5.61 (br s, 2H)

2,2-Dibromo-N-(2,6-dinitro-4-trifluoromethylphenyl)-2-fluoroacetamidine (hereinafter referred to as present compound 23)

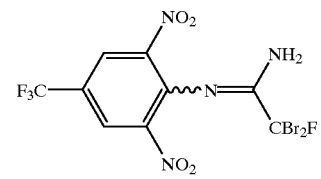

¹H-NMR (250 MHz, CDCl₃/TMS): δ (ppm)=8.40 (s, 2H), 5.33 (br s, 2H)

2-Bromo-N-(2,6-dinitro-4-trifluoromethylphenyl)-2-fluoroacetamidine (hereinafter referred to as present compound 24)

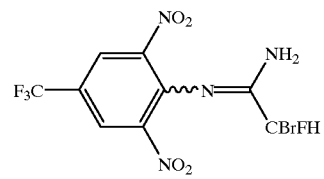

¹H-NMR (250 MHz, CDCl₃/TMS): δ (ppm)=8.36 (s, 2H), 6.85 (d, J=49.8 Hz, 1H), 5.35 (br s, 2H)

2-Bromo-2,2-difluoro-N-(2,6-dinitro-4-trifluoromethylphenyl) acetamidine (hereinafter referred to as present compound 25)

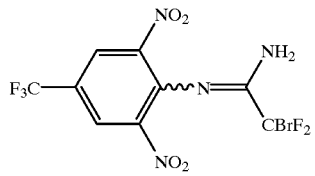

¹H-NMR (300 MHz, CDCl₃/TMS): δ (ppm)=8.41 (s, 2H), 5.39 (br s, 2H)

N-(2,6-Dinitro-4-trifluoromethylphenyl)-2,2,3,3-tetrafluoropropionamidine (hereinafter referred to as present compound 26)

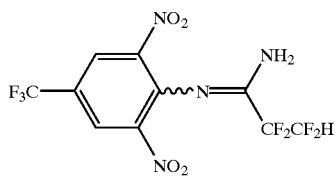

¹H-NMR (250 MHz, CDCl₃/TMS): δ (ppm)=8.40 (s, 2H), 6.17 (tt, J=52.7 Hz, J=5.7 Hz, 1H), 5.53 (br s, 2H)

N-(2-Bromo-6-nitro-4-trifluoromethylphenyl)-2,2,3,3,3-pentafluoropropionamidine (hereinafter referred to as present compound 27)

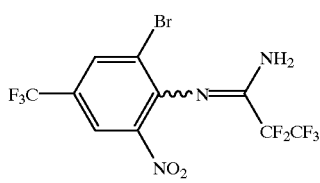

¹H-NMR (300 MHz, CDCl₃/TMS): δ (ppm)=8.19 (s, 1H), 8.09 (s, 1H), 5.28 (br s, 2H)

2-Chloro-2,2-difluoro-N-(2,6-dinitro-4-trifluoromethylphenyl)acetamidine (hereinafter referred to as present compound 28)

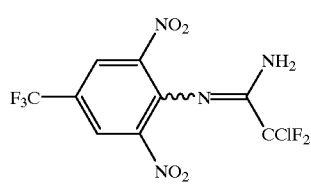

¹H-NMR (250 MHz, CDCl₃/TMS): δ (ppm)=8.42 (s, 2H), 5.44 (br s, 2H)

2-Bromo-N-(2,6-dinitro-4-trifluoromethylphenyl)-2,3,3,3-tetrafluoropropionamidine (hereinafter referred to as present compound 29)

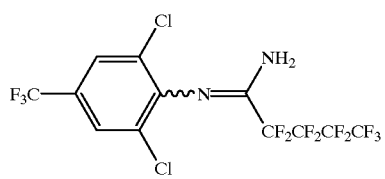

¹H-NMR (300 MHz, CDCl₃/TMS): δ (ppm)=8.38 (s, 2H), 5.46 (br s, 2H)

N-(2,6-Dichloro-4-trifluoromethylphenyl)-2,2,3,3,4,4,5,5,5-nonafluoropentanamidine (hereinafter referred to as present compound 30)

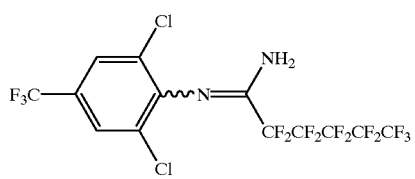

¹H-NMR (250 MHz, CDCl₃/TMS): δ (ppm)=7.62 (s, 2H), 5.08 (br s, 2H)

N-(2,6-Dichloro-4-trifluoromethylphenyl)-2,2,3,3,4,4,5,5,6,6,6-undecafluorohexanamidine (hereinafter referred to as present compound 31)

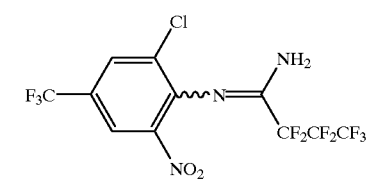

¹H-NMR (250 MHz, CDCl₃/TMS): δ (ppm)=7.62 (s, 2H), 5.07 (br s, 2H)

N-(2-Chloro-6-nitro-4-trifluoromethylphenyl)-2,2,3,3,4,4,4-heptafluorobutyramidine (hereinafter referred to as present compound 32)

¹H-NMR (250 MHz, CDCl₃/TMS): δ (ppm)=8.12 (s, 1H), 7.92 (s, 1H), 5.28 (br s, 2H)

N-(2,6-Dinitro-4-trifluoromethylphenyl)-2,2,2-trifluoroacetamidine (hereinafter referred to as present compound 33)

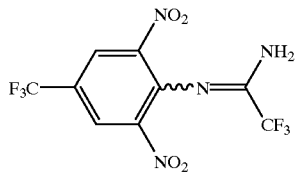

¹H-NMR (300 MHz, CDCl₃/TMS): δ (ppm)=8.41 (s, 2H), 5.42 (br s, 2H)

2,2-Dichloro-N-(2,6-dinitro-4-trifluoromethylphenyl)-2-fluoroacetamidine (hereinafter referred to as present compound 34)

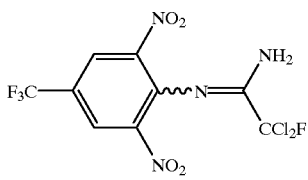

¹H-NMR (300 MHz, CDCl₃/TMS): δ (ppm)=8.41 (s, 2H), 5.37 (br s, 2H)

3-Chloro-N-(2,6-dinitro-4-trifluoromethylphenyl)-2,2,3,3-tetrafluoropropionamidine (hereinafter referred to as present compound 35)

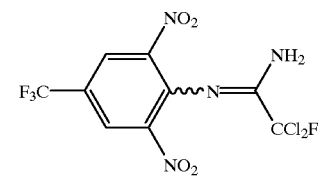

¹H-NMR (250 MHz, CDC₁₃/TMS): δ (ppm)=8.39 (s, 2H), 5.48 (br s, 2H)

2,2-Difluoro-N-(2,6-dinitro-4-trifluoromethylphenyl)propionamidine (hereinafter referred to as present compound 36)

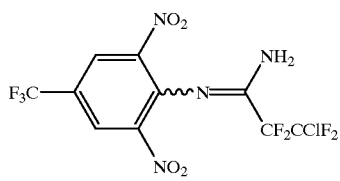

¹H-NMR (300 MHz, CDCl₃/TMS): δ (ppm)=8.38 (s, 2H), 5.28 (br s, 2H), 1.92 (t, J=19.1 Hz, 3H)

3,4-Dichloro-N-(2,6-dinitro-4-trifluoromethylphenyl)-2,2,3,4,4-pentafluorobutyramidine (hereinafter referred to as present compound 37)

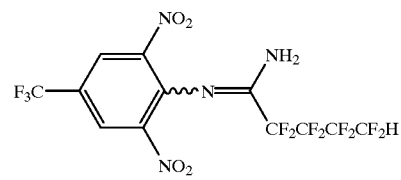

¹H-NMR (300 MHz, CDCl₃/TMS): δ (ppm)=8.36 (s, 2H), 5.49 (br s, 2H)

N-(2,6-Dinitro-4-trifluoromethylphenyl)-2,2,3,3,4,4,5,5-octafluoropentanamidine (hereinafter referred to as present compound 38)

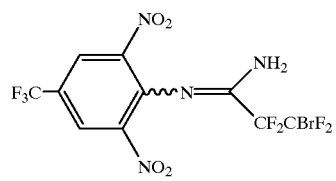

¹H-NMR (250 MHz, CDCl₃/TMS): δ (ppm)=8.39 (s, 2H), 6.09 (tt, J=51.9 Hz, J=5.3 Hz, 1H), 5.50 (br s, 2H)

3-Bromo-N-(2,6-dinitro-4-trifluoromethylphenyl)-2,2,3,3-tetrafluoropropionamidine (hereinafter referred to as present compound 39)

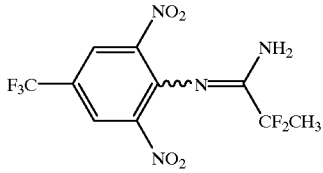

¹H-NMR (250 MHz, CDCl₃/TMS): δ (ppm)=8.39 (s, 2H), 5.59 (br s, 2H)

3-Bromo-2-chloro-N-(2,6-dinitro-4-trifluoromethylphenyl)-2,3,3-trifluoropropionamidine (hereinafter referred to as present compound 40)

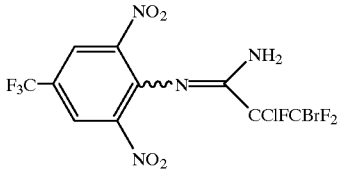

¹H-NMR (250 MHz, CDCl₃/TMS): δ (ppm)=8.36 (s, 2H), 5.49 (br s, 2H)

N-(2, 6-Dinitro-4-trifluoromethylphenyl)-2-methoxy-2,3,3,3-tetrafluoropropionamidine (hereinafter referred to as present compound 41)

¹H-NMR (300 MHz, CDCl₃/TMS): δ (ppm)=8.33 (s, 2H), 5.52 (br s, 2H), 3.73 (s, 3H)

N-(2,6-Dinitro-4-pentafluoroethylphenyl)-2,2,3,3,4,4,4-heptafluorobutyramidine (hereinafter referred to as present compound 42)

¹H-NMR (300 MHz, CDCl₃/TMS): δ (ppm)=8.35 (s, 2H), 5.54 (br s, 2H)

N-(2,6-Dinitro-4-pentafluoroethylphenyl)-2,2,3,3,3-pentafluoropropionamidine (hereinafter referred to as present compound 43)

¹H-NMR (300 MHz, CDCl₃/TMS): δ (ppm)=8.37 (s, 2H), 5.56 (br s, 2H)

N-(2,6-Dinitro-4-trifluoromethylphenyl)-2,2,3,4,4,4-hexafluorobutyramidine (hereinafter referred to as present compound 44)

¹H-NMR (250 MHz, CDCl₃/TMS): δ (ppm)=8.40 (s, 2H), 5.60–5.25 (m, 1H), 5.54 (br s, 2H)

N-(2,6-Dinitro-4-trifluoromethoxyphenyl)-2,2,3,3,4,4,4-heptafluorobutyramidine (hereinafter referred to as present compound 45)

¹H-NMR (250 MHz, CDCl₃/TMS): δ (ppm)=8.04 (s, 2H), 5.50 (br s, 2H)

N-(2,6-Dinitro-4-trifluoromethylphenyl)-2,2-difluoro-2-ethylthioacetamidine (hereinafter referred to as present compound 46)

¹H-NMR (300 MHz, CDCl₃/TMS): δ (ppm)=8.38 (s, 2H), 5.37 (br s, 2H), 2.98 (q, J=7.5 Hz, 2H), 1.39 (t, J=7.5 Hz, 3H)

N-(2,6-Dinitro-4-heptafluoropropylphenyl)-2,2,3,3,3-pentafluoropropionamidine (hereinafter referred to as present compound 47)

¹H-NMR (300 MHz, CDCl₃/TMS): δ (ppm)=8.36 (s, 2H), 5.52 (br s, 2H)

N-(2,6-Dinitro-4-heptafluoropropylphenyl)-2,2,3,3,4,4,4-heptafluorobutyramidine (hereinafter referred to as present compound 48)

¹H-NMR (300 MHz, CDCl₃/TMS): δ (ppm)=8.34 (s, 2H), 5.55 (br s, 2H)

N-(2,6-Dinitro-4-heptafluoropropylphenyl)-2,2,2-trifluoroacetamidine (hereinafter referred to as present compound 49)

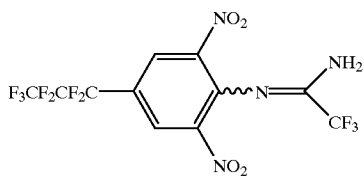

$^1$H-NMR (300 MHz, CDCl$_3$/TMS): δ (ppm)=8.37 (s, 2H), 5.48 (br s, 2H)

N-{2,6-Dinitro-4-(1,2,2,2-tetrafluoro-1-trifluoromethylethyl)phenyl}-2,2,3,3,4,4,4-heptafluorobutyramidine (hereinafter referred to as present compound 50)

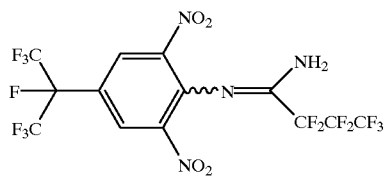

$^1$H-NMR (300 MHz, CDCl$_3$/TMS): δ (ppm)=7.58 (s, 2H), 5.10 (b)r s, 2H)

N-(2,6-Dinitro-4-trifluoromethylphenyl)-2,2-difluoro-2-methylthioacetamidine (hereinafter referred to as present compound 51)

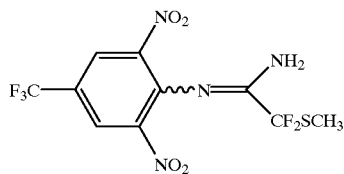

$^1$H-NMR (250 MHz, CDCl$_3$/TMS): δ (ppm)=8.39 (s, 2H), 5.38 (br s, 2H), 2.40 (s, 3H)

Production Example 3

First, 0.34 g (1.0 mmol) of N-(2,6-dichloro-4-trifluoromethylphenyl)-2,2,2-trifluoroacetoimidoyl chloride was dissolved in 10 ml of N,N-dimethylformamide, to which 0.08 g (1.0 mmol) of dimethylamine hydrochloride and 0.22 g (2.0 mmol) of triethylamine, and the mixture was stirred at room temperature for 3 hours. Water was poured into the reaction mixture, which was extracted with ethyl acetate. The organic layer was dried over anhydrous magnesium sulfate and then concentrated under reduced pressure to give 0.28 g of N'-(2,6-dichloro-4-trifluoromethylphenyl)-2,2,2-trifluoro-N,N-dimethylacetamidine (hereinafter referred to as present compound 52).

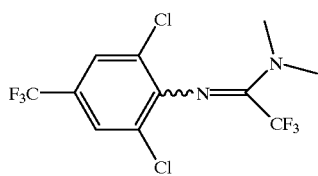

$^1$H-NMR (250 MHz, CDCl$_3$/TMS): δ (ppm)=7.51 (s, 2H), 3.16 (s, 6H)

Compounds obtained in the same manner as described in Production Example 3 and their NMR data are shown below.

N'-(2,6-Dichloro-4-trifluoromethylphenyl)-2,2,3,3,3-pentafluoro-N,N-dimethylpropionamidine (hereinafter referred to as present compound 53)

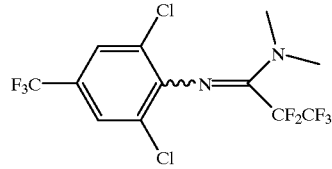

$^1$H-NMR (300 MHz, CDCl$_3$/TMS): δ (ppm)=7.52 (s, 2H), 2.87 (s, 6H)

2-Chloro-N'-(2,6-dichloro-4-trifluoromethylphenyl)-2,2-difluoro-N,N-dimethylacetamidine (hereinafter referred to as present compound 54)

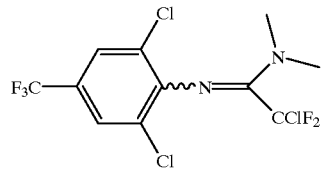

$^1$H-NMR (300 MHz, CDCl$_3$/TMS): δ (ppm)=7.50 (s, 2H), 3.18 (s, 6H)

N'-(2,6-Dichloro-4-trifluoromethylphenyl)-2,2,2-trifluoro-N-methylacetamidine (hereinafter referred to as present compound 55)

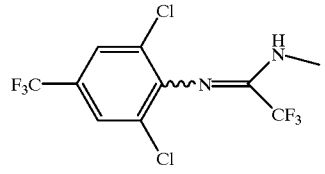

$^1$H-NMR (250 MHz, CDCl$_3$/TMS): δ (ppm)=7.53 (s, 2H), 5.48 (br s, 1H), 2.95 (d, J=4.9 Hz, 3H)

Production Example 4

First, 0.17 g (0.50 mmol) of N-(2,6-dichloro-4-trifluoromethylphenyl)-2,2,2-trifluoroacetoimidoyl chloride was dissolved in 10 ml of N,N-dimethyl formamide, to which 0.10 g (0.50 mmol) of dipropylamine and 0.10 g (0.50 mmol) of triethylamine were added, and the mixture was stirred at room temperature for 3 hours. Water was poured into the reaction mixture, which was extracted with ethyl acetate. The organic layer was dried over anhydrous magnesium sulfate and then concentrated under reduced pressure to give 0.18 g of N'-(2,6-dichloro-4-trifluoromethylphenyl)-2,2,2-trifluoro-N,N-dipropylacetamidine (hereinafter referred to as present compound 56).

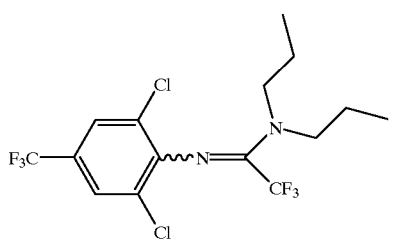

$^1$H-NMR (300 MHz, CDCl$_3$/TMS): δ (ppm)=7.50 (s, 2H), 3.39 (t, J=7.7 Hz, 4H), 1.75 (tq, J=7.7 Hz, J=7.4 Hz, 4H), 0.94 (t, J=7.4 Hz, 6H)

Compounds obtained in the same manner as described in Production Example 4 and their NMR data are shown below.

N'-(2,6-Dichloro-4-trifluoromethylphenyl)-N,N-diethyl-2,2,2-trifluoroacetamidine (hereinafter referred to as present compound 57)

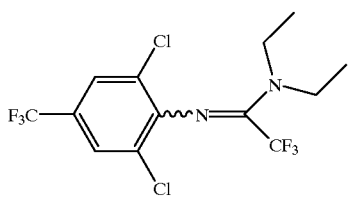

$^1$H-NMR (250 MHz, CDCl$_3$/TMS): δ (ppm)=7.50 (s, 2H), 3.52 (q, J=7.0 Hz, 4H), 1.29 (t, J=7.0 Hz, 6H)

N'-(2,6-Dichloro-4-trifluoromethylphenyl)-2,2-dichloro-N-ethylacetamidine (hereinafter referred to as present compound 58)

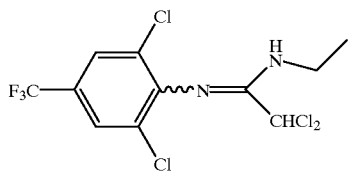

$^1$H-NMR (250 MHz, CDCl$_3$/TMS): γ (ppm)=7.56 (s, 2H), 5.86 (s, 1H), 5.70–5.48 (m, 1H), 3.50 (qd, J=7.2 Hz, J=5.6 Hz, 2H), 1.33 (t, J=7.2 Hz, 3H)

2,2-Dichloro-N'-(2,6-dinitro-4-trifluoromethylphenyl)-N-ethylacetamidine (hereinafter referred to as present compound 59)

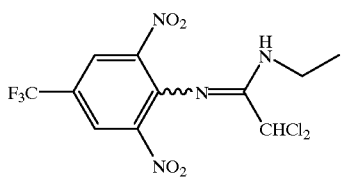

$^1$H-NMR (250 MHz, CDCl$_3$/TMS): δ (ppm)=8.37 (s, 2H), 6.03 (s, 1H), 6.03–5.86 (m, 1H), 3.42 (qd, J=7.2 Hz, J=5.5 Hz, 2H), 1.29 (t, J=7.2 Hz, 3H)

Production Example 5

First, 0.18 g (0.50 mmol) of N-(2,6-dichloro-4-trifluoromethylphenyl)-2,2,3,3,3-pentafluoropropionamidine as present compound 4 was dissolved in 10 ml of N,N-dimethylformamide, to which 0.04 g (1.0 mmol) of sodium hydride (about 60% in oil) was added under ice cooling, and the mixture was stirred for 10 minutes. Then, 0.05 g (0.50 mmol) of methyl chloroformate was added to the reaction mixture, which was stirred at room temperature for 6 hours. Water was poured into the reaction mixture, which was extracted with ethyl acetate. The organic layer was washed with saturated sodium chloride solution, dried over anhydrous magnesium sulfate, and then concentrated under reduced pressure. The residue was subjected to silica gel column chromatography to give 0.08 g of [1-(2,6-dichloro-4-trifluoromethylphenylimino)-2,2,3,3,3-pentafluoropropyl]carbamic acid methyl ester (hereinafter referred to as present compound 60).

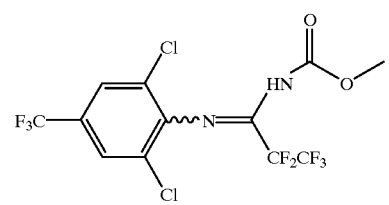

$^1$H-NMR (300 MHz, CDCl$_3$/TMS): δ (ppm)=7.56 (s, 2H), 7.45 (br s, 1H), 3.61 (s, 3H)

Production Example 6

In the same manner as described in Example 5, except that 0.05 g of methyl chloroformate was replaced by 0.04 g of acetyl chloride, 0.11 g of N-[1-(2,6-dichloro-4-trifluoromethylphenylimino)-2,2,3,3,3-pentafluoropropyl]-acetamide (hereinafter referred to as present compound 61) was obtained.

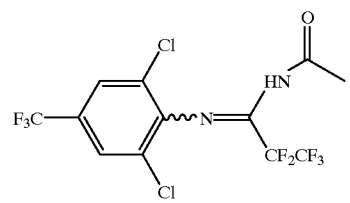

$^1$H-NMR (300 MHz, CDCl$_3$/TMS): δ (ppm)=7.80 (br s, 1H), 7.55 (s, 2H), 2.11 (s, 3H)

Reference Production Example 1

First, 9.1 g (50 mmol) of 2,2,3,4,4,4-hexafluorobutan-1-ol was dissolved in 40 ml of water, to which 14.7 g (50 mmol) of potassium dichromate and 17 ml of concentrated sulfuric acid, and the mixture was heated at 100° C. for 3 hours. After cooling, the reaction mixture was extracted with diethyl ether. The organic layer was dried over anhydrous magnesium sulfate and then concentrated under reduced pressure to give 9.0 g of 2,2,3,4,4,4-hexafluorobutyric acid.

$^1$H-NMR (250 MHz, CDCl$_3$/TMS): δ (ppm)=5.80 (br s, 1H), 5.36–5.06 (m, 1H)

Reference Production Example 2

To a solution of 7.0 g (31 mmol) of 3-bromo-2,2,3,3-tetrafluoropropionic acid in 40 ml of ethanol was added 1.0 ml of concentrated sulfuric acid, and the mixture was heated under reflux for 8 hours and then distilled under ordinary pressure to give an ethanolic solution of ethyl 3-bromo-2,2,3,3-tetrafluoropropionate. Ammonia gas was blown into the solution, which was left at room temperature overnight and then concentrated under reduced pressure to give 5.6 g of 3-bromo-2,2,3,3-tetrafluoropropionamide as a white solid.

$^1$H-NMR (250 MHz, CDCl$_3$/TMS): δ (ppm)=6.40 (br s, 2H)

Reference Production Example 3

First, 4.7 g (27 mmol) of bromodifluoroacetamide was dissolved in 20 ml of N,N-dimethylacetamide, to which 3.2 g (46 mmol) of methyl mercaptan sodium salt was added, and the mixture was heated at 80° C. for 2 days. Water was poured into the reaction mixture, which was extracted with ethyl acetate. The organic layer was dried over anhydrous magnesium sulfate and then concentrated under reduced pressure. The residue was subjected to silica gel column chromatography to give 4.3 g of 2,2-difluoro-2-(methylthio) acetamide.

$^1$H-NMR (300 MHz, CDCl$_3$/TMS): δ (ppm)=6.20 (br s, 1H), 5.76 (br s, 1H), 2.38 (s, 3H)

Reference Production Example 4

First, 4.6 g (20 mmol) of 2,2-dichloro-4-trifluoromethylaniline was dissolved in 100 ml of dichloromethane, to which 6.2 g (20 mmol) of pentafluoropropionic anhydride was added under ice cooling, and the mixture was stirred at room temperature for 18 hours. The solvent was distilled out under reduced pressure, followed by addition of hexane to the residue, and the precipitated solids were collected by filtration. The resulting solids were washed with hexane and then dried to give 4.3 g of N-(2,6-dichloro-4-trifluoromethylphenyl)-2,2,3,3,3-pentafluoropropionamide.

$^1$H-NMR (250 MHz, CDCl$_3$/TMS): δ (ppm) 7.80 (br s, 1H), 7.72 (s, 2H)

Reference Production Example 5

First, 4.6 g (17 mmol) of 2-chloro-1,3-dinitro-5-trifluoromethylbenzene and 4.0 g (18 mmol) of 3-bromo-2,2,3,3-tetrafluoropropionamide were dissolved in 40 ml of acetone, to which 5.0 g (36 mmol) of potassium carbonate was added, and the mixture was heated under reflux for 4 hours. Water was poured into the reaction mixture, which was extracted with ethyl acetate. The organic layer was dried over anhydrous magnesium sulfate and then concentrated under reduced pressure. The residue was subjected to silica gel column chromatography to give 3-bromo-N-(2,6-dinitro-4-trifluoromethylphenyl)-2,2,3,3-tetrafluoropropionamide.

$^1$H-NMR (300 MHz, CDCl$_3$/TMS): δ (ppm)=10.60 (br s, 1H), 8.66 (s, 2H)

Reference Production Example 6

First, 6 ml of concentrated sulfuric acid was added to 1.0 g (4.4 mmol) of 1-methoxy-4-pentafluoroethylbenzene, to which 1.8 ml of fuming nitric acid was added dropwise under ice cooling at a temperature of 10° C. or lower over 10 minutes. After completion of the dropwise addition, the mixture was stirred for 30 minutes. The reaction mixture was poured into ice water, which was then extracted with ethyl acetate. The organic layer was dried over anhydrous magnesium sulfate and then concentrated under reduced pressure. The residue was subjected to silica gel column chromatography to give 2-methoxy-1,3-dinitro-5-pentafluoroethylbenzene.

$^1$H-NMR (300 MHz, CDCl$_3$/TMS): δ (ppm)=8.26 (s, 2H), 4.15 (s, 3H)

Reference Production Example 7

First, 0.70 g (2.2 mmol) of 2-methoxy-1,3-dinitro-5-pentafluoroethylbenzene and 0.47 g (2.2 mmol) of 2,2,3,3,4,4,4-heptafluorobutylamide were dissolved in 7 ml of acetone, to which 0.61 g (4.4 mmol) of potassium carbonate was added, and the mixture was heated under reflux for 2 hours. The reaction mixture was poured into water, which was extracted with ethyl acetate. The organic layer was dried over anhydrous magnesium sulfate and then concentrated under reduce pressure. The residue was subjected to silica gel column chromatography to give N-(2,6-dinitro-4-pentafluoroethylphenyl)-2,2,3,3,4,4,4-heptafluorobutylamide.

$^1$H-NMR (250 MHz, CDCl$_3$/TMS): δ (ppm)=8.63 (s, 2H)

Reference Production Example 8

A mixture of 0.41 g (1.0 mmol) of 3-chloro-N-(2,6-dinitro-4-trifluoromethylphenyl)-2,2,3,3-tetrafluoropropionamide, 0.31 g (1.5 mmol) of phosphorous pentachloride, and 2 ml of toluene was heated under reflux for 6 hours. The reaction mixture was poured into saturated aqueous sodium hydrogencarbonate solution, which was extracted with ethyl acetate. The organic layer was washed with saturated aqueous sodium chloride solution, dried over anhydrous magnesium sulfate, and then concentrated under reduced pressure. The residue was subjected to silica gel column chromatography to give 3-chloro-N-(2,6-dinitro-4-trifluoromethylphenyl)-2,2,3,3-tetrafluoropropionimidoyl chloride.

$^1$H-NMR (300 MHz, CDC$_{13}$/TMS): δ (ppm)=8.68 (s, 2H)

Reference Production Example 9

First, 4.3 g (11 mmol) of N-(2,6-dichloro-4-trifluoromethylphenyl)-2,2,3,3,3-pentafluoropropionamide was dissolved in 22 ml of dichloromethane, to which 1.8 ml of carbon tetrachloride and 4.5 g (17 mmol) of triphenylphosphine were added at room temperature, and the mixture was stirred for 18 hours. The reaction mixture was concentrated under reduced pressure, followed by addition of hexane, and undissolved matter was removed by filtration, and the filtrate was concentrated under reduced pressure. The residue was subjected to silica gel column chromatography to give 3.8 g of N-(2,6-dichloro-4-trifluoromethylphenyl)-2,2,3,3,3-pentafluoropropionimidoyl chloride.

$^1$H-NMR (300 MHz, CDCl$_3$/TMS): δ (ppm) 7.67 (s, 2H)

Reference Production Example 10

First, 31.4 g (120 mmol) of triphenylphosphine and 4.9 g (48 mmol) of triethylamine were added to 20 ml of carbon tetrachloride, to which 3.8 g (40 mmol) of difluoroacetic acid was added dropwise under ice cooling. After completion of the dropwise addition, the mixture was stirred under ice cooling for 10 minutes. Then, a solution of 9.2 g (40 mmol) of 2,6-dichloro-4-trifluoromethylaniline in 20 ml of carbon tetrachloride was added dropwise to the reaction mixture, which was heated at 80° C. for 6 hours. The reaction mixture was concentrated under reduced pressure, followed by addition of hexane, and undissolved matter was removed by filtration. The filtrate was concentrated under reduced pressure. The residue was subjected to silica gel column chromatography to give 6.0 g of N-(2,6-dichloro-4-trifluoromethylphenyl)-2,2-difluoroacetimidoyl chloride.

$^1$H-NMR (300 MHz, CDCl$_3$/TMS): δ (ppm)=7.65 (s, 21), 6.38 (t, J=54.1 Hz, 1H)

The following will describe some formulation examples where parts are by weight and the present compounds are designated by their compound numbers.

Formulation Example 1

Ten parts of each of present compounds 1 to 61, 35 parts of white carbon containing 50 parts of polyoxyethylene alkyl ether sulfate ammonium salt, and 55 parts of water are mixed and wet pulverized to give a flowable of each compound.

Formulation Example 2

Fifty parts of each of present compounds 1 to 61, 3 parts of calcium lignin sulfonate, 2 parts of sodium lauryl sulfate, and 45 parts of synthetic hydrated silicon oxide are well pulverized and mixed to give a wettable powder of each compound.

Formulation Example 3

Twenty five parts of each of present compounds 1 to 61, 3 parts of polyoxyethylene sorbitan monooleate, 3 parts of CMC (carboxymethylcellulose), and 69 parts of water are mixed and wet pulverized until the mean particle size comes to 5 μm or smaller to give a flowable of each compound.

Formulation Example 4

Two parts of each of present compounds 1 to 61, 88 parts of kaolin clay, and 10 parts of talc are well pulverized and mixed to give a dust of each compound.

Formulation Example 5

Twenty of each of present compounds 1 to 61, 14 parts of polyoxyethylene styryl phenyl ether, 6 parts of calcium dodecylbenzenesulfonate, and 60 parts of xylene are well mixed to give an emulsifiable concentrate of each compound.

Formulation Example 6

Two parts of each of present compounds 1 to 61, 1 part of synthetic hydrated silicon oxide, 2 parts of calcium lignin sulfonate, 30 parts of bentonite, and 65 parts of kaolin clay are well pulverized and mixed. The mixture is well kneaded with the addition of water, followed by granulation and drying to give a granule of each compound.

Formulation Example 7

Twenty parts of each of present compounds 1 to 61 and 1.5 parts of sorbitan trioleate are mixed with 28.5 parts of an aqueous solution containing 2 parts of polyvinyl alcohol. The mixture is then pulverized to a mean particle size of 3 μm or smaller using a sand grinder. This is followed by the addition of 40 parts of an aqueous solution containing 0.05 part of xanthan gum and 0.1 part of aluminum magnesium silicate and by the subsequent addition of 10 parts of propylene glycol. The mixture is stirred to give a 20% aqueous suspension of each compound.

Formulation Example 8

First, 0.1 part of each of compounds 1 to 61 is dissolved in 5 parts of xylene and 5 parts of trichloroethane. The solution is mixed with 89.9 parts of deodorized kerosine to give a 0.1% oil spray of each compound.

Formulation Example 9

First, 0.1 part of each of present compounds 1 to 61, 0.2 part of tetramethrin, 0.1 part of d-phenothrin, 10 parts of trichloroethane, and 59.6 parts of deodorized kerosine are mixed to complete dissolution. The solution is put in an aerosol vessel. The vessel is then equipped with a valve, through which 30 parts of a propellant (liquefied petroleum gas) is charged under increased pressure to give an oil-based aerosol of each compound.

Formulation Example 10

An aerosol vessel is filled with a mixture of 0.2 part of each of present compounds 1 to 61, 0.1 part of d-allethrin, 0.2 part of d-phenothrin, 5 parts of xylene, 3.4 parts of deodorized kerosine, and 1 part of an emulsifier (ATMOS 300 available from Atlas Chemical Co.); and 50 parts of pure water. The vessel is then equipped with a valve, through which 40 parts of a propellant (liquefied petroleum gas) is charged under increased pressure to give a water-based aerosol of each compound.

Formulation Example 11

First, 0.3 g of each of present compounds 1 to 61 is mixed with 0.3 g of d-allethrin, which is dissolved in 20 ml of acetone. The solution is then uniformly mixed with 99.4 g of a carrier for mosquito-coils (prepared by mixing Tabu powder, pyrethrum marc powder and wood flour in the ratio of 4:3:3) under stirring. The mixture is well kneaded with the addition of 120 ml of water, followed by molding and drying to give a mosquito-coil of each compound.

Formulation Example 12

First, 0.4 g of each of present compounds 1 to 61, 0.4 part of d-allethrin, and 0.4 g of pipenyl butoxide are dissolved in acetone to have a total volume of 10 ml. Then, 0.5 ml of the solution is uniformly absorbed in a substrate for electric mosquito-mats having a size of 2.5 cm×1.5 cm and a thickness of 0.3 cm (prepared by forming a fibrillated mixture of cotton linter and pulp into a sheet) to give an electric mosquito-mat of each compound.

Formulation Example 13

First, 100 mg of each of present compounds 1 to 61 is dissolved in a suitable amount of acetone. The solution is absorbed in a porous ceramic plate with a size of 4.0 cm×4.0 cm and a thickness of 1.2 cm to give a heating smoke formulation of each compound.

Formulation Example 14

First, 10 mg of each of present compounds 1 to 61 is dissolved in 0.5 ml of acetone, and the solution is added to and uniformly mixed with 5 g of solid feed powder for animals (Breeding Solid Feed Powder CE-2 available from Japan Clea Co., Ltd.). The acetone is then removed by air drying to give a 5% poison bait of each compound.

Formulation Example 15

Each of present compounds 1 to 61 is diluted with acetone, and the dilution is absorbed in a nonwoven fabric by dropping so that the ratio comes to 1 g per square meter. The acetone is then removed by air drying to give an anti-acarine sheet of each compound.

Formulation Example 16

Each of present compounds 1 to 61 is diluted with acetone, and the dilution is absorbed in a filter paper by dropping so that the ratio comes to 1 g per square meter. The acetone is then removed by air drying to give an anti-acarine sheet of each compound.

Formulation Example 17

Five parts of each of present compounds 1 to 61 is mixed with 95 parts of diethylene glycol monoethyl ether to give a 5% spot-on formulation of each compounds.

The following test examples are provided for demonstrating that the present compounds are useful as active ingredients of pesticides. In these test examples, the present compounds are designated by their compound numbers as described above.

Compounds used for comparison are as follows:

Compound 17 disclosed in JP-A 3-264557, ie., N'-(2,6-dichlorophenyl)-2,2,2-trifluoromethyl-N-methylacetamidine (hereinafter referred to as comparative compound A)

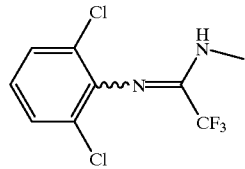

Compound 168 disclosed in JP-A 56-81553, i.e., 2,2-dichloro-N-ethyl-N'-(2,4,6-trichlorophenyl)acetamidine (hereinafter referred to as comparative compound B)

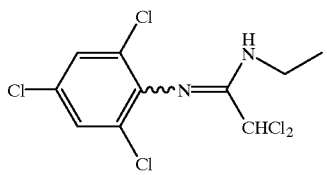

Compound 139 disclosed in JP-A 56-81553, i.e., 2,2-dichloro-N-ethyl-N'-(2-nitro-4-trifluoromethylphenyl)acetamidine (hereinafter referred to as comparative compound C)

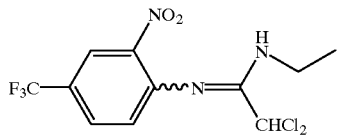

Test Example 1

A 20 µg/µl solution of each of present compounds 55, 58, and 59 and comparative compounds A, B, and C in acetone was applied in an amount of 1 µl to the sternal prothorax of some female adults of German cockroach (*Blattella germanica*), to which a bait (rat-bleeding solid feed available from Oriental Yeast Industry Co., Ltd.) and water were fed. After 7 days, their survival was examined to determine the mortality (ten adults in one group, triplicate). As a result, it was found that present compounds 55, 58, and 59 exhibited a mortality of 90% or higher, whereas comparative compounds A, B, and C exhibited a mortality of 25% or lower.

Test Example 2

On the bottom of a polyethylene cup of 5.5 cm in diameter was placed a filter paper of the same size, to which a water dilution (500 ppm) of each of the formulations obtained from present compounds 1, 2, 3, 4, 5, 6, 7, 8, 9, 10, 11, 12, 13, 14, 15, 16, 17, 18, 19, 20, 21, 25, 26, 27, 28, 29, 30, 32, 33, 34, 35, 36, 37, 38, 39, 40, 41, 42, 43, 44, 45, 47, 49, 50, 51, 52, 53, 54, 55, 56, 57, 58, 59, 60, and 61 according to Formulation Example 1 was added dropwise in an amount of 0.7 ml, and the cup was uniformly charged with 30 mg of sucrose as a bait. Two male adults of German cockroach (*Blattella germanica*) were set free in each cup, which was then kept covered. After 6 days, their survival was examined to determine the mortality. As a result, it was found that present compounds 1, 2, 3, 4, 5, 6, 7, 8, 9, 10, 11, 12, 13, 14, 15, 16, 17, 18, 19, 20, 21, 25, 26, 27, 28, 29, 30, 32, 33, 34, 35, 36, 37, 38, 39, 40, 41, 42, 43, 44, 45, 47, 49, 50, 51, 52, 53, 54, 55, 56, 57, 58, 59, 60, and 61 exhibited the mortality of 100%

Test Example 3

On the bottom of a polyethylene cup of 5.5 cm in diameter was placed a filter paper of the same size, to which a water dilution (500 ppm) of each of the formulations obtained from present compounds 1, 2, 3, 4, 5, 6, 7, 8, 9, 10, 11, 12, 13, 14, 15, 16, 17, 18, 19, 20, 21, 25, 26, 27, 28, 29, 32, 33, 34, 35, 36, 37, 38, 39, 40, 41, 42, 43, 44, 45, 47, 51, 52, 53, 54, 55, 60, and 61 according to Formulation Example 1 was added dropwise in an amount of 0.7 ml, and the cup was uniformly charged with about 30 mg of sucrose as a bait. Ten female adults of house fly (*Musca domeestica*) were set free in each cup, which was then kept covered. After 1 day, their survival was examined to determine the mortality. As a result, it was found that present compounds 1, 2, 3, 4, 5, 6, 7, 8, 9, 10, 11, 12, 13, 14, 15, 16, 17, 18, 19, 20, 21, 25, 26, 27, 28, 29, 32, 33, 34, 35, 36, 37, 38, 39, 40, 41, 42, 43, 44, 45, 47, 51, 52, 53, 54, 55, 60, and 61 exhibited the mortality of 100%

Test Example 4

A water dilution (500 ppm) of each of the formulations obtained from present compounds 3, 4, 5, 6, 8, 9, 10, 11, 12, 13, 14, 15, 16, 17, 18, 19, 20, 21, 25, 26, 27, 28, 29, 30, 31, 32, 34, 35, 36, 37, 38, 39, 40, 41, 42, 43, 44, 45, 47, 48, 49, 50, 51, 53, 54, 55, 57, 58, 59, 60, and 61 according to Formulation Example 1 was added in an amount of 0.7 ml to ion-exchanged water (the concentration of active ingredient was 3.5 ppm). Twenty final-instar larvae of common mosquito (*Culex pipiens pallens*) were set free in each solution. After 8 days, their survival was examined to determine the mortality. As a result, it was found that present compounds 3, 4, 5, 6, 8, 9, 10, 11, 12, 13, 14, 15, 16, 17, 18, 19, 20, 21, 25, 26, 27, 28, 29, 30, 31, 32, 34, 35, 36, 37, 38, 39, 40, 41, 42, 43, 44, 45, 47, 48, 49, 50, 51, 53, 54, 55, 57, 58, 59, 60, and 61 exhibited the mortality of 100%

What is claimed is:

1. An amidine compound of formula I:

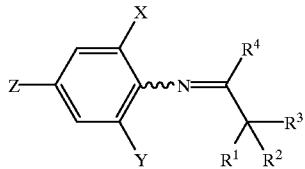

wherein X and Y are the same or different and are independently halogen, nitro, cyano, or $C_1$–$C_6$ alkyl; Z is $C_1$–$C_6$ haloalkyl or $C_1$–$C_6$ haloalkoxy; $R^1$ is hydrogen, halogen, $C_1$–$C_6$ alkyl, $C_1$–$C_6$ haloalkyl, $C_1$–$C_6$ alkoxy, $C_1$–$C_6$ haloalkoxy, or a group of formula: $S(O)_n$—$R^5$ (wherein $R^5$ is $C_1$–$C_8$ alkyl or $C_1$–$C_6$ haloalkyl; and n is 0, 1, or 2); $R^2$ and $R^3$ are the same or different and are independently halogen or $C_1$–$C_6$ haloalkyl; and $R^4$ is a group of formula: $NR^6R^7$ or $N=CR^8R^9$ (wherein $R^6$ is hydrogen, $C_1$–$C_6$ alkyl, ($C_1$–$C_6$ alkoxy)-carbonyl, ($C_1$–$C_6$ alkoxy) $C_1$–$C_6$ alkyl, or $C_2$–$C_6$ acyl; $R^7$ is hydrogen, $C_1$–$C_6$ alkyl, ($C_1$–$C_6$ alkoxy) carbonyl, or $C_2$–$C_6$ acyl; $R^8$ is $C_1$–$C_6$ alkyl or hydrogen; and $R^9$ is $C_1$–$C_6$ alkoxy, $C_1$–$C_6$ alkyl, or di($C_1$–$C_6$ alkyl)amino).

2. The amidine compound according to claim 1, wherein $R^4$ is amino.

3. The amidine compound according to claim 1, wherein $R^1$ is $C_1$–$C_6$ haloalkyl, $R^2$ and $R^3$ are the same or different and are independently halogen.

4. The amidine compound according to claim 1, wherein $R^1$ is $C_1$–$C_6$ haloalkyl, $R^2$ and $R^3$ are the same or different and are independently halogen, and $R^4$ is amino.

5. The amidine compound according to claim 1, wherein $R^1$ is $C_1$–$C_6$ haloalkyl; $R^2$ and $R^3$ are the same or different and are independently halogen; $R^4$ is amino; X and Y are the same or different and are independently halogen or nitro.

6. The amidine compound according to claim 5, wherein Z is trifluoromethyl.

7. A pesticide comprising an amidine compound according to claim 1 as an active ingredient and a carrier.

8. A method for the control of pests, which comprises applying a pesticidally effective amount of an amidine compound according to claim 1 to pests or their habitats.

* * * * *